United States Patent
Valenta et al.

(10) Patent No.: US 8,859,210 B2
(45) Date of Patent: Oct. 14, 2014

(54) METHOD FOR IDENTIFYING ALLERGENIC PROTEINS AND PEPTIDES

(75) Inventors: Rudolph Valenta, Vienna (AT); Ric Van Tol, Nijmegen (NL); Udo Herz, Kirchhain (DE); Heidrun Hochwallner, St. Leonhard/Forst (AT); Margarte Focke-Tejkl, Vienna (AT); Ines Swoboda, Vienna (AT); Ulrike Schulmeister, Waldhausen (AT)

(73) Assignee: Mead Johnson Nutrition Company, Glenview, IL (US)

( * ) Notice: Subject to any disclaimer, the term of this patent is extended or adjusted under 35 U.S.C. 154(b) by 756 days.

(21) Appl. No.: 12/581,108

(22) Filed: Oct. 16, 2009

(65) Prior Publication Data

US 2010/0143262 A1 Jun. 10, 2010

Related U.S. Application Data

(60) Provisional application No. 61/196,416, filed on Oct. 17, 2008.

(51) Int. Cl.
*G01N 33/53* (2006.01)
*G01N 33/68* (2006.01)

(52) U.S. Cl.
CPC ........ *G01N 33/6854* (2013.01); *G01N 2800/24* (2013.01); *G01N 2500/00* (2013.01)
USPC ...................................................... 435/7.1

(58) Field of Classification Search
None
See application file for complete search history.

(56) References Cited

U.S. PATENT DOCUMENTS

| | | | |
|---|---|---|---|
| 6,238,925 B1 * | 5/2001 | Sampson | 436/23 |
| 6,799,121 B2 | 9/2004 | Chu et al. | |
| 2002/0168373 A1 * | 11/2002 | Thomas et al. | 424/184.1 |

OTHER PUBLICATIONS

Groenen et al. 'Characterization of a GlyCAM1-like gene (glycosylation-dependent cell adhesion molecule 1) which is highly and specifically expressed in the lactating bovine mammary gland.' Gene, 158:189-195, 1995.*
Chen et al. 'On the allergenicity of Hev b 1 among health care workers and patients with spina bifida allergic to natural rubber latex.' J. Allergy Clin Immunol. 100:684-693, 1997.*
Vila et al. 'Role of conformational and linear epitope in the achievement of tolerance in cow's milk allergy.' Clin. Exp. Allerg. 31:1599-1606, 2001.*
Ball, et al., Isolation of an Immunodominant IgE Hapten from an Epitope Expression cDNA Library, The Journal of Biological Chemistry, vol. 269, No. 45, Nov. 11, 1994, pp. 28323-28328.
Budde, et al., The Stripped Basophil Histamine Release Bioassay as a Tool for the Detection of Allergen-Specific IgE in Serum, Int Arch Allergy Immunol., 2001; 126:277-285.
Figeys, et al., Protein Identification by Capillary Zone Electrophoresis/Microelectrospray Ionization-Tandem Mass Spectrometry at the Subfemtomole Level, Anal. Chem., 1996, 68, 1822-1828.
Focke, et al., Nonanaphylactic synthetic peptides derived from B cell epitopes of the major grass pollen allergen, Phl p. 1, for allergy vaccination, The FASEB Journal, published online Jul. 24, 2001.
Hunt, et al., Protein sequencing by tandem mass spectrometry, Proc. Natl. Acad. Sci. USA, vol. 83, Sep. 1986, pp. 6233-6237.
Jarvinen, et al. Specficity of IgE antibodies to sequential epitopes of hen's egg ovomucoid as a marker for persistence of egg allergy, Allergy, 2007: 62: 758-765.
Jarvinen, et al., IgE and IgG Binding Epitopes on α-Lactalbumin and β-Lactoglobulin in Cow's Milk Allergy, Int. Ach. Allergy Immunol., 2001; 126:111-118.
Schulmeister, et al., Cloning, Expression, and Mapping of Allergenic Determinants of [alpha]S1-Casein, a Major Cow's Milk Allergen, J Immunol., 2009; 182;7019-7029.
Shevchenko, et al., Linking genome and proteome by mass spectrometry: Large-scale identification of yeast proteins from two dimensional gels, Proc. Natl. Acad. Sci. USA, vol. 93, pp. 14440-14445, Dec. 1996.
Vrtala, et al., Conversion of the Major Birch Pollen Allergen, Bet v 1, into Two Nonanaphylactic T Cell Epitope-containing Fragments, J. Clin. Invest., vol. 99, No. 7, Apr. 1997, 1673-1681.
Wilm, et al., Femtomole sequencing of proteins from polyacrylamide gels by nano-electrospray mass spectrometry, Nature, vol. 379, Feb. 1, 1996, pp. 466-469.
Batt, et al., Expression of Recombinant Bovine Beta-Lactoglobulin in *Escherichia coli*, Agric. Biol. Chem., 54 (4), 949-955, 1990.
Blanc, et al., Update on optimized purification and characterization of natural milk allergens, Mol. Nutr. Food Res., 2008, 52, S166-S175.
Chatel, et al., Expression, Purification and Immunochemical Characterization of Recombinant Bovine Beta-Lactoglobulin, a Major Cow Milk Allergen, Molecular Immunology, vol. 3, No. 14, pp. 1113-1118, 1996.
Massimo, et al., Cow's milk allergens identified by two-dimensional immunoblotting and mass spectrometry, Mol. Nutr. Food Res., 2004, 48, 363-369.
Monaci, et al., Milk allergens, their characteristics and their detection in food: A review, Eur. Food Res. Technol., (2006) 223: 149-179.
Rhyner et al., Cloning allergens via phage display, Methods, 32 (2004) 212-218.

(Continued)

*Primary Examiner* — Nora Rooney
(74) *Attorney, Agent, or Firm* — Waddey & Patterson, P.C.; James R. Cartiglia

(57) ABSTRACT

A method for identifying allergenic proteins and peptides. More specifically, a method for identifying allergenic milk proteins and/or peptides including the steps of: providing at least one expression library comprising DNA or cDNA derived from the mammary gland tissue of a lactating cow, expressing at least one protein or peptide encoded by said expression library, determining the binding capacity of said at least one protein or peptide to IgE of at least one serum of an individual who is sensitive to cow's milk, contacting the at least one protein or peptide exhibiting an IgE binding capacity as determined in step c) with basophil cells, eosinophil cells or mast cells and identifying the at least one protein or peptide as being allergenic when said basophil cells, eosinophil cells or mast cells release upon contact with at least one protein or peptide of step d) at least one mediator.

13 Claims, 13 Drawing Sheets

(56) References Cited

OTHER PUBLICATIONS

Vrtala, et al., cDNA Cloning of a Major Allergen from Timothy Grass (Phleum pretense) Pollen; Characterization of the Recombinant Phl p V Allergen, The Journal of Immunology, vol. 151, 4773-4781, No. 9, Nov. 1, 1993.

Weghofer, et al., Characterization of Der p 21, a new important allergen derived from the gut of house dust mites, Allergy, 2008: 63: 758-767.

* cited by examiner

```
        110       120       130       140       150       160       170       180       190       200       210 214
RYLGYLEQLLRLKKYKVPQLEYVPNSAEERLHSMKEGIHAQQKEPMIGVNQELAYFYPELFRQFYQLDAYPSGAWYYVPLGTQYTDAPSFSDIPNPIGSENSEKTTMPLW
                                                                                                              214
     121                                                                                                      214
                                                                                                              214
                                                                                                              214
                                                                                                              214
                                                                                                              214
                                                                                                              214
                                                                                                              214
                                                                                                              214
                                                                                                              214
                                                                                                              214
                                                                                                              214
                                                                                                              214
 104                                                                                                          214
   107                                                                                                        214
     111                                                                                                      214
          119                                                                                                 214
               132                                                                                            214
                 136                                                                                          214
                   138                                                                                        214
                       145                                                                                    214
                          148                                                                                 214
                                157                                                                           214
                                      171                                                                     214
                                             184                                                              214
                                                                                                202    214
                              143
            123
         118
                                          165                                                       209 214
            122             137                                                                             214

110       120       130       140       150       160       170       180       190       200       210       220
PQYLQYLYQGPIVLNPWDQVKRNAVPITPTLNREQLSTSEENSKKTVDMESTEVFTKKTKLTEEEKNRLNFLKKISQRYQKFALPQYLKTVYQHQKAMKPWIQPKTKVIPYVRYL
                                                                                                                      222
                                                                                                                      222
```

Fig. 1A
continued beta-casein

```
              1    10    20    30    40    50    60    70    80    90   100
              MKVLILACLVALALARELEELNVPGEIVESLSSSEESITRINKKIEKFQSEEQQQTEDELQDKIHPFAQTQSLVYPFPGPIPNSLPQNIPPLTQTPVVVPPFLQPEVM
full length   1                        cas b-3                              cas b-2           cas b-4
    17.6      1
   18.03      1                                                                             90
   15.19      1                                                                            88
   15.34      1                                                                          85
    17.9      1                                                                          84
    16.3      1                                                                        80
   18.10      1                                                                    74
   15.31      1                                                              66
   15.11      1                                                             65
    18.7      2
   15.17      2                                                                         84
    18.4      2                                                                                   97
   15.22            20                                                   69
   9.199             24
   15.36                     31                                                    80
    18.1                                                             63                         99
    25.6                                                              65
    18.5                                                                 71
    17.5                                                                                            100
    18.9                                                                                            100
``` kappa-casein

```
              1    10    20    30    40    50    60    70    80    90   100
              MMKSFFLVVTILALTLPFLGAQEQNQEQPIRCEKDERFFSDKIAKYIPIQYVLSRYPSYGLNYYQQKPVALINNQFLPYPYYAKPAAVRSPAQILQWQVLSNTV
full length   1
   15.28      1
    19.2      2                                                                                  94
    2.33
   12.117
```

Matchline to Figure 1B continued

Fig. 1B

Fig. 1B
continued alpha-lactalbumin

```
        1        10        20        30        40        50        60        70        80        90
        |         |         |         |         |         |         |         |         |         |
        MSFVSLLLVGILFHATQAEQLTKCEVFRELKDLKGYGGVSLPEWVCTTFHTSGYDTQAIVQNNDSTEYGLFQINNKIWCKDDQNPHSSNICNISCDKFLD
``` bovine serum albumin

```
        1        10        20        30        40        50        60        70        80        90
        |         |         |         |         |         |         |         |         |         |
        MKWVTFISLLLLFSSAYSRGVFRRDTHKSEIAHRFKDLGEEHFKGLVLIAFSQYLQQCPFDEHVKLVNELEFAKTCVADESHAGCEKSLHTLFGDE
       210       220       230       240       250       260       270       280       290
        |         |         |         |         |         |         |         |         |
        KIETMREKVLTSSARQRLRCASIQKFGERALKAWSVARLSQKFPKAEFVEVTKLVTDLTKVHKECCHGDLLECADDRADLAKYICDNQDTISSKL
       410       420       430       440       450       460       470       480       490
        |         |         |         |         |         |         |         |         |
        EPQNLIKQNCDQFEKLGEYGFQNALIVRYTRKVPQVSTPTLVEVSRSLGKVGTRCCTKPESERMPCTEDYLSLILNRLCVLHEKTPVSEKVTKC
``` lactoferrin

```
        1        10        20        30        40        50        60        70        80        90
        |         |         |         |         |         |         |         |         |         |
        MKLFVPALLSLGALGLCLAAPRKNVRWCTISQPEWFKCRRWQWRMKKLGAPSITCVRRAFALECIRAIAEKKADAVTLDGGMVFEAGRDPYKLR
       210       220       230       240       250       260       270       280       290
        |         |         |         |         |         |         |         |         |
        ACSSREPYFGYSGAFKCLQDGAGDVAFVKETTVFENLPEKADRDQYELLCLNNSRAPVDAFKECHLAQVPSHAVVARSSVDGKEDLIWKLLSKAQ
       410       420       430       440       450       460       470       480       490
        |         |         |         |         |         |         |         |         |
        VLVLKGEADALNLDGGYIYTAGKCGLVPVLAENRKSSKHSSLDCVLRPTEGYLAVAVVKKANEGLTWNSLKDKKSCHTAVDRTAGWNIPMGLIVNQ
       610       620       630       640       650       660       670       680
        |         |         |         |         |         |         |         |
        TEAQSCHLAVAPNHAVVSRSDRAAHVKQVLLHQQALFGKNGKNCPDKFCLFKSETKNLLFNDNTECLAKLGGRPTYEEYLGTEYV
```

Matchline to Figure 1C continued

Fig. 1C

```
       |100    110    120    130    140
       |   |     |     |     |     |
       DDLTDDIMCVKKILDKVGINYWLAHKALCSEKLDQWLCEKL
```

```
       |100    110    120    130    140    150    160    170    180    190    200
       |   |     |     |     |     |     |     |     |     |     |     |
       LCKVASLRETYGDMADCCEKQEPERNECFLSHKDDSPDLPKLKPDPNTLCDEFKADEKKFWGKYLYEIARRHPYFYAPELLYYANKYNGVFQECCQAEDKGACLLP
       |300    310    320    330    340    350    360    370    380    390    400
       |   |     |     |     |     |     |     |     |     |     |
       KECCDKPLLEKSHCIAEVEKDAIPENLPPLTADFAEDKDVCKNYQEAKDAFLGSFLYEYSRRHPEYAVSVLLRLAKEYEATLEECCAKDDPHACYSTVFDLLKHLVD
       |500   510    520    530    540    550    560    570    580    590    600   606
       |   |    |     |     |     |     |     |     |     |     |     |     |
       CTESLVNRRPCFSALTPDETYVPKAFDEKLFTFHADICTLPDTEKQIKKQTALVELLKHKPKATEEQLKTVMENFVAFVDKCCAADDKEACFAVEGPKLVVSTQTALA
```

Matchline to Figure 1C

```
       |100    110    120    130    140    150    160    170    180    190    200
       |   |     |     |     |     |     |     |     |     |     |     |
       PVAAEIYGTKESPQTHYYAVAVVKKGSNFQLDQLQGRKSCHTGLGRSAGWIIPMGILRPYLSWTESLEPLQGAVAKFFSASCVPCIDRQAYPNLCQLCKGEGENQC
       |300    310    320    330    340    350    360    370    380    390    400
       |   |     |     |     |     |     |     |     |     |     |     |
       EKFGKNKSRSFQLFGSPPGQRDLLFKDSALGFLRIPSKVDSALYLGSRYLTTLKNLRETAEEVKARYTRVVWCAVGPEEQKKCQQWSQQSGQNVTCATASTTDDCI
       |500    510    520    530    540    550    560    570    580    590    600
       |   |     |     |     |     |     |     |     |     |     |     |
       TGSCAFDEFFSQSCAPGADPKSRLCALCAGDDQGLDKCVPNSKEKYYGYTGAFRCLAEDVGDVAFVKNDTVWENTNGESTADWAKNLNREDFRLLCLDGTRKPV
       |690    700    708
       |   |     |     |
       TAIANLKKCSTSPLLEACAFLTR
```

Fig. 1C
continued

| Milk component | Name | MW (kDa) |
|---|---|---|
| purified proteins | | |
| α-casein | Bos d 8 alpha | 25.5 (αS1) 26 (αS2) |
| β-casein | Bos d 8 beta | 24.0 |
| κ-casein | Bos d 8 kappa | 19.0 |
| α-lactalbumin | Bos d 4 | 14.2 |
| β-lactoglobulin, variant A | Bos d 5 A | 18.3 |
| β-lactoglobulin, variant B | Bos d 5 B | 18.3 |
| lactoferrin | Bos d lactoferrin | 80 |
| bovine serum albumin | Bos d 6 | 66.3 |
| sheep serum abumin | Ovi a SSA | 24.3 |
| human α-lactalbumin | Hom s lactalbumin | 16.2 |
| milk fractions | | |
| cow casein | Bos d 8 | 19 - 26 |
| sheep casein | Ovi a casein | 24.3 |
| goat casein | Cap h casein | 24.3 |
| recombinant proteins | | |
| ταS1-casein | Bos d 8 alphaS1 | 23.9 |
| ταS2-casein | Bos d 8 alphaS2 | 25.3 |
| τβ-casein | Bos d 8 beta | 24.5 |
| τκ-casein | Bos d 8 kappa | 19.9 |
| τα-lactalbumin | Bos d 4 | 19.2 |
| τβ-lactoglobulin | Bos d 5 B | 15.1 |
| recombinant fragments | | |
| BSA fragment 1, AA 1-190 | | 23.9 |
| BSA fragment 2, AA 200-389 | | 22.6 |
| BSA fragment 3, AA390-590 | | 23.4 |
| αS1-casein peptides | | |
| Cas1, AA 1-31 | | 3.8 |
| Cas2, AA 32-64 | | 3.8 |
| Cas3, AA 65-100 | | 4.3 |
| Cas4, AA 101-133 | | 3.9 |
| Cas5, AA 134-167 | | 4.2 |
| Cas6, AA 168-199 | | 3.6 |
| α-lactalbumin peptides | | |
| Lac1, AA 1-19 | | 2.3 |
| Lac2, AA 15-34 | | 2.2 |
| Lac3, AA 30-49 | | 2.2 |
| Lac4, AA 45-64 | | 2.4 |
| Lac5, AA 60-79 | | 2.3 |
| Lac6, AA 75-94 | | 2.3 |
| Lac7, AA 90-109 | | 2.3 |
| Lac8, AA 105-123 | | 2.2 |
| whole milk samples | | |
| cow's milk | Bos d | |
| sheep's milk | Ovi a | |
| goat's milk | Cap h | |
| mare's milk | Equ c | |
| human milk | Hom s | |

Matchline to Figure 6b

Fig. 4a

| Function | Preparation | Reference |
|---|---|---|
| calcium phophate transport | natural purified | Stewart A.F. et al., 1984, X00564 |
| calcium phophate transport | natural purified | Stewart A.F. et al., 1987, M16644 |
| calcium phophate transport | natural purified | Baev A.A. et al., 1987, M16645 |
| regulatory subunit of lactose synthase | natural purified | Alexander L.J. et al., 1988, X14907 |
| lipocalin, binds retinol | natural purified | Vilotte J.-L., 1987, 18780 |
| lipocalin, binds retinol | natural purified | Oliviera K.M. et al., 2001, 1QG5_A |
| transferrin, iron binding transport proteins | natural purified | Braunitzer G, et al., 1973, X14712 |
| regulation of osmotic pressure of blood | natural purified | Pierce A. et al., 1991, X57084 |
| regulation of osmotic pressure of blood | natural purified | unpublished, M73993 |
| regulatory subunit of lactose synthase | natural purified | Brown W.M. et al., 1989, CAA34903 |
| | | Hall L. et al., 1982, J00270 |
| calcium phophate transport | natural purified | Stewart A.F. et al., 1984, X00564 |
| | | Stewart A.F. et al., 1987, M16644 |
| | | Baev A.A. et al., 1987, M16645 |
| | | Alexander L.J. et al., 1988, X14907 |
| calcium phophate transport | natural purified | Baev A.A. et al., 1987, M16645 |
| calcium phophate transport | natural purified | Alexander L.J. et al., 1988, X14907 |
| calcium phophate transport | recombinant, His-tagged | |
| calcium phophate transport | recombinant, His-tagged | |
| calcium phophate transport | recombinant, His-tagged | |
| calcium phophate transport | recombinant, His-tagged | |
| regulatory subunit of lactose synthase | recombinant, His-tagged | |
| lipocalin, binds retinol | recombinant, His-tagged | |
| | recombinant, His-tagged | |
| | recombinant, His-tagged | |
| | recombinant, His-tagged | |
| | synthesized | |
| | synthesized | |
| | synthesized | |
| | synthesized | |
| | synthesized | |
| | synthesized | |
| | synthesized | |
| | synthesized | |
| | synthesized | |
| | synthesized | |
| | synthesized | |
| | synthesized | |
| | synthesized | |
| | synthesized | |

Matchline to Figure 6a

Fig. 4b

Mascot Search Results
Protein View
Match to: CASB_BOVIN Score: 144
Beta-casein precursor - Bos taurus (Bovine)
Found in search of D:\Data\milk 0.3171.07.mgf
Nominal mass (Mr): 25149; Calculated pI value: 5.26
NCBI BLAST search of CASB_BOVIN against nr
Unformatted sequence string for pasting into other applications
Taxonomy: Bos taurus
Fixed modifications: Carboxymethyl (C)
Variable modifications: Oxidation (M)
No enzyme cleavage specificity Sequence Coverage: 11%

Matched peptides shown in Bold
```
  1 MKVLILACLV ALALARELEE LNVPGEIVES LSSSEESITR INKKIEKFQS
 51 EEQQQTEDEL QDKIHPFAQT QSL VYPFPGP IPNSLPQNIP PLTQT  PVVVP
101 P FLQPEVMGV SKVKEAMAPK HKEMPFPKYP VEPFTESQSL TLTDVENLHL
151 PLPLLQSWM H QPHQPLPPTV MFPPQSVLSL SQSKVLPVPQ KAVPYPQRDM
201 PIQAFLLYQE PVLGPVRGPF PIIV
```

Fig. 6

```
                         SEQUENCE LISTING

<160> NUMBER OF SEQ ID NOS: 84

<210> SEQ ID NO 1
<211> LENGTH: 32
<212> TYPE: PRT
<213> ORGANISM: Bos taurus

<400> SEQUENCE: 1

Arg Pro Lys His Pro Ile Lys His Gln Gly Leu Pro Gln Glu Val Leu
1               5                   10                  15

Asn Glu Asn Leu Leu Arg Phe Phe Val Ala Pro Phe Pro Glu Val Cys
            20                  25                  30

<210> SEQ ID NO 2
<211> LENGTH: 33
<212> TYPE: PRT
<213> ORGANISM: Bos taurus

<400> SEQUENCE: 2

Phe Gly Lys Glu Lys Val Asn Glu Leu Ser Lys Asp Ile Gly Ser Glu
1               5                   10                  15

Ser Thr Glu Asp Gln Ala Met Glu Asp Ile Lys Gln Met Glu Ala Glu
            20                  25                  30

Ser

<210> SEQ ID NO 3
<211> LENGTH: 36
<212> TYPE: PRT
<213> ORGANISM: Bos taurus

<400> SEQUENCE: 3

Ile Ser Ser Ser Glu Glu Ile Val Pro Asn Ser Val Glu Gln Lys His
1               5                   10                  15

Ile Gln Lys Glu Asp Val Pro Ser Glu Arg Tyr Leu Gly Tyr Glu Gln
            20                  25                  30

Leu Leu Arg Cys
        35

<210> SEQ ID NO 4
<211> LENGTH: 34
<212> TYPE: PRT
<213> ORGANISM: Bos taurus

<400> SEQUENCE: 4

Cys Leu Lys Lys Tyr Lys Val Pro Gln Leu Glu Ile Val Pro Asn Ser
1               5                   10                  15

Ala Glu Glu Arg Leu His Ser Met Lys Glu Gly Ile His Ala Gln Gln
            20                  25                  30
```

Lys Glu

<210> SEQ ID NO 5
<211> LENGTH: 35
<212> TYPE: PRT
<213> ORGANISM: Bos taurus

<400> SEQUENCE: 5

Cys Pro Met Ile Gly Val Asn Gln Glu Leu Ala Tyr Phe Tyr Pro Glu
1               5                   10                  15

Leu Phe Arg Gln Phe Tyr Gln Leu Asp Ala Tyr Pro Ser Gly Ala Trp
            20                  25                  30

Tyr Tyr Val
        35

<210> SEQ ID NO 6
<211> LENGTH: 33
<212> TYPE: PRT
<213> ORGANISM: Bos taurus

<400> SEQUENCE: 6

Pro Leu Gly Thr Gln Tyr Thr Asp Ala Pro Ser Phe Ser Asp Ile Pro
1               5                   10                  15

Asn Pro Ile Gly Ser Glu Asn Ser Glu Lys Thr Thr Met Pro Leu Trp
            20                  25                  30

Cys

<210> SEQ ID NO 7
<211> LENGTH: 205
<212> TYPE: PRT
<213> ORGANISM: Bos taurus

<400> SEQUENCE: 7

Met Arg Gly Val Phe Arg Arg Asp Thr His Lys Ser Glu Ile Ala His
1               5                   10                  15

Arg Phe Lys Asp Leu Gly Glu Glu His Phe Lys Gly Leu Val Leu Ile
            20                  25                  30

Ala Phe Ser Gln Tyr Leu Gln Gln Cys Pro Phe Asp Glu His Val Lys
        35                  40                  45

Leu Val Asn Glu Leu Thr Glu Phe Ala Lys Thr Cys Val Ala Asp Glu
    50                  55                  60

Ser His Ala Gly Cys Glu Lys Ser Leu His Thr Leu Phe Gly Asp Glu
65                  70                  75                  80

Leu Cys Lys Val Ala Ser Leu Arg Glu Thr Tyr Gly Asp Met Ala Asp
                85                  90                  95

Cys Cys Glu Lys Gln Glu Pro Glu Arg Asn Glu Cys Phe Leu Ser His
            100                 105                 110

Lys Asp Asp Ser Pro Asp Leu Pro Lys Leu Lys Pro Asp Pro Asn Thr
        115                 120                 125

Leu Cys Asp Glu Phe Lys Ala Asp Glu Lys Lys Phe Trp Gly Lys Tyr
    130                 135                 140

Leu Tyr Glu Ile Ala Arg Arg His Pro Tyr Phe Tyr Ala Pro Glu Leu
145                 150                 155                 160

Leu Tyr Tyr Ala Asn Lys Tyr Asn Gly Val Phe Gln Glu Cys Cys Gln
                165                 170                 175

Ala Glu Asp Lys Gly Ala Cys Leu Leu Pro Lys Ile Glu Thr Met Arg
            180                 185                 190

```
Glu Lys Val Leu Thr Ser Ser His His His His His
            195             200             205
```

<210> SEQ ID NO 8
<211> LENGTH: 197
<212> TYPE: PRT
<213> ORGANISM: Bos taurus

<400> SEQUENCE: 8

```
Met Ala Arg Gln Arg Leu Arg Cys Ala Ser Ile Gln Lys Phe Gly Glu
1               5                   10                  15

Arg Ala Leu Lys Ala Trp Ser Val Ala Arg Leu Ser Gln Lys Phe Pro
            20                  25                  30

Lys Ala Glu Phe Val Glu Val Thr Lys Leu Val Thr Asp Leu Thr Lys
        35                  40                  45

Val His Lys Glu Cys Cys His Gly Asp Leu Leu Glu Cys Ala Asp Asp
    50                  55                  60

Arg Ala Asp Leu Ala Lys Tyr Ile Cys Asp Asn Gln Asp Thr Ile Ser
65                  70                  75                  80

Ser Lys Leu Lys Glu Cys Cys Asp Lys Pro Leu Leu Glu Lys Ser His
                85                  90                  95

Cys Ile Ala Glu Val Glu Lys Asp Ala Ile Pro Glu Asn Leu Pro Pro
            100                 105                 110

Leu Thr Ala Asp Phe Ala Glu Asp Lys Asp Val Cys Lys Asn Tyr Gln
        115                 120                 125

Glu Ala Lys Asp Ala Phe Leu Gly Ser Phe Leu Tyr Glu Tyr Ser Arg
    130                 135                 140

Arg His Pro Glu Tyr Ala Val Ser Val Leu Leu Arg Leu Ala Lys Glu
145                 150                 155                 160

Tyr Glu Ala Thr Leu Glu Glu Cys Cys Ala Lys Asp Asp Pro His Ala
                165                 170                 175

Cys Tyr Ser Thr Val Phe Asp Lys Leu Lys His Leu Val Asp Glu His
            180                 185                 190

His His His His His
        195
```

<210> SEQ ID NO 9
<211> LENGTH: 208
<212> TYPE: PRT
<213> ORGANISM: Bos taurus

<400> SEQUENCE: 9

```
Met Pro Gln Asn Leu Ile Lys Gln Asn Cys Asp Gln Phe Glu Lys Leu
1               5                   10                  15

Gly Glu Tyr Gly Phe Gln Asn Ala Leu Ile Val Arg Tyr Thr Arg Lys
            20                  25                  30

Val Pro Gln Val Ser Thr Pro Thr Leu Val Glu Val Ser Arg Ser Leu
        35                  40                  45

Gly Lys Val Gly Thr Arg Cys Cys Thr Lys Pro Glu Ser Glu Arg Met
    50                  55                  60

Pro Cys Thr Glu Asp Tyr Leu Ser Leu Ile Leu Asn Arg Leu Cys Val
65                  70                  75                  80

Leu His Glu Lys Thr Pro Val Ser Glu Lys Val Thr Lys Cys Cys Thr
                85                  90                  95

Glu Ser Leu Val Asn Arg Arg Pro Cys Phe Ser Ala Leu Thr Pro Asp
            100                 105                 110
```

```
Glu Thr Tyr Val Pro Lys Ala Phe Asp Glu Lys Leu Phe Thr Phe His
            115                 120                 125
Ala Asp Ile Cys Thr Leu Pro Asp Thr Glu Lys Gln Ile Lys Lys Gln
        130                 135                 140
Thr Ala Leu Val Glu Leu Leu Lys His Lys Pro Lys Ala Thr Glu Glu
145                 150                 155                 160
Gln Leu Lys Thr Val Met Glu Asn Phe Val Ala Phe Val Asp Lys Cys
                165                 170                 175
Cys Ala Ala Asp Asp Lys Glu Ala Cys Phe Ala Val Glu Gly Pro Lys
            180                 185                 190
Leu Val Val Ser Thr Gln Thr Ala Leu Ala His His His His His His
            195                 200                 205
```

```
<210> SEQ ID NO 10
<211> LENGTH: 11
<212> TYPE: PRT
<213> ORGANISM: Bos taurus

<400> SEQUENCE: 10

His Gln Pro His Gln Pro Leu Pro Pro Thr Val
1               5                   10

<210> SEQ ID NO 11
<211> LENGTH: 11
<212> TYPE: PRT
<213> ORGANISM: Bos taurus

<400> SEQUENCE: 11

Val Tyr Pro Phe Pro Gly Pro Ile Pro Asn Ser
1               5                   10

<210> SEQ ID NO 12
<211> LENGTH: 6
<212> TYPE: PRT
<213> ORGANISM: Bos taurus

<400> SEQUENCE: 12

Leu Ser Ser Ser Glu Glu
1               5

<210> SEQ ID NO 13
<211> LENGTH: 8
<212> TYPE: PRT
<213> ORGANISM: Bos taurus

<400> SEQUENCE: 13

Pro Val Val Val Pro Pro Phe Leu
1               5

<210> SEQ ID NO 14
<211> LENGTH: 19
<212> TYPE: PRT
<213> ORGANISM: Bos taurus

<400> SEQUENCE: 14

Glu Gln Leu Thr Lys Cys Glu Val Phe Arg Glu Leu Lys Asp Leu Lys
1               5                   10                  15

Gly Tyr Gly

<210> SEQ ID NO 15
<211> LENGTH: 20
<212> TYPE: PRT
```

<213> ORGANISM: Bos taurus

<400> SEQUENCE: 15

Leu Lys Gly Tyr Gly Val Ser Leu Pro Glu Trp Val Cys Thr Thr
1               5                   10                  15

Phe His Thr Ser
            20

<210> SEQ ID NO 16
<211> LENGTH: 20
<212> TYPE: PRT
<213> ORGANISM: Bos taurus

<400> SEQUENCE: 16

Thr Phe His Thr Ser Gly Tyr Asp Thr Gln Ala Ile Val Gln Asn Asn
1               5                   10                  15

Asp Ser Thr Glu
            20

<210> SEQ ID NO 17
<211> LENGTH: 20
<212> TYPE: PRT
<213> ORGANISM: Bos taurus

<400> SEQUENCE: 17

Asn Asp Ser Thr Glu Tyr Gly Leu Phe Gln Ile Asn Asn Lys Ile Trp
1               5                   10                  15

Cys Lys Asp Asp
            20

<210> SEQ ID NO 18
<211> LENGTH: 20
<212> TYPE: PRT
<213> ORGANISM: Bos taurus

<400> SEQUENCE: 18

Trp Cys Lys Asp Asp Gln Asn Pro His Ser Ser Asn Ile Cys Asn Ile
1               5                   10                  15

Ser Cys Asp Lys
            20

<210> SEQ ID NO 19
<211> LENGTH: 20
<212> TYPE: PRT
<213> ORGANISM: Bos taurus

<400> SEQUENCE: 19

Ile Ser Cys Asp Lys Phe Leu Asp Asp Asp Leu Thr Asp Asp Ile Met
1               5                   10                  15

Cys Val Lys Lys
            20

<210> SEQ ID NO 20
<211> LENGTH: 20
<212> TYPE: PRT
<213> ORGANISM: Bos taurus

<400> SEQUENCE: 20

Met Cys Val Lys Lys Ile Leu Asp Lys Val Gly Ile Asn Tyr Trp Leu
1               5                   10                  15

Ala His Lys Ala
            20

```
<210> SEQ ID NO 21
<211> LENGTH: 19
<212> TYPE: PRT
<213> ORGANISM: Bos taurus

<400> SEQUENCE: 21

Leu Ala His Lys Ala Leu Cys Ser Glu Lys Leu Asp Gln Trp Leu Cys
1               5                   10                  15

Glu Lys Leu

<210> SEQ ID NO 22
<211> LENGTH: 214
<212> TYPE: PRT
<213> ORGANISM: Bos taurus

<400> SEQUENCE: 22

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
            20                  25                  30

Glu Asn Leu Leu Arg Phe Phe Val Ala Pro Phe Pro Glu Val Phe Gly
        35                  40                  45

Lys Glu Lys Val Asn Glu Leu Ser Lys Asp Ile Gly Ser Glu Ser Thr
    50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Gln Leu Glu Ile Val Pro
        115                 120                 125

Asn Ser Ala Glu Glu Arg Leu His Ser Met Lys Glu Gly Ile His Ala
    130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175

Gly Ala Trp Tyr Tyr Val Pro Leu Gly Thr Gln Tyr Thr Asp Ala Pro
            180                 185                 190

Ser Phe Ser Asp Ile Pro Asn Pro Ile Gly Ser Glu Asn Ser Glu Lys
        195                 200                 205

Thr Thr Met Pro Leu Trp
    210

<210> SEQ ID NO 23
<211> LENGTH: 121
<212> TYPE: PRT
<213> ORGANISM: Bos taurus

<400> SEQUENCE: 23

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
            20                  25                  30

Glu Asn Leu Leu Arg Phe Phe Val Ala Pro Phe Pro Glu Val Phe Gly
```

```
            35                  40                  45
Lys Glu Lys Val Asn Glu Leu Ser Lys Asp Ile Gly Ser Glu Ser Thr
         50                  55                  60

Glu Asp Gln Ala Met Glu Asp Ile Lys Gln Met Glu Ala Glu Ser Ile
 65                  70                  75                  80

Ser Ser Ser Glu Glu Ile Val Pro Asn Ser Val Glu Gln Lys His Ile
                 85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val
            115                 120

<210> SEQ ID NO 24
<211> LENGTH: 208
<212> TYPE: PRT
<213> ORGANISM: Bos taurus

<400> SEQUENCE: 24

Thr Cys Leu Val Ala Val Ala Leu Ala Arg Pro Lys His Pro Ile Lys
  1               5                  10                  15

His Gln Gly Leu Pro Gln Glu Val Leu Asn Glu Asn Leu Leu Arg Phe
             20                  25                  30

Phe Val Ala Pro Phe Pro Glu Val Phe Gly Lys Glu Lys Val Asn Glu
         35                  40                  45

Leu Ser Lys Asp Ile Gly Ser Glu Ser Thr Glu Asp Gln Ala Met Glu
 50                  55                  60

Asp Ile Lys Gln Met Glu Ala Glu Ser Ile Ser Ser Ser Glu Glu Ile
 65                  70                  75                  80

Val Pro Asn Ser Val Glu Gln Lys His Ile Gln Lys Glu Asp Val Pro
                 85                  90                  95

Ser Glu Arg Tyr Leu Gly Tyr Leu Glu Gln Leu Leu Arg Leu Lys Lys
            100                 105                 110

Tyr Lys Val Pro Gln Leu Glu Ile Val Pro Asn Ser Ala Glu Glu Arg
            115                 120                 125

Leu His Ser Met Lys Glu Gly Ile His Ala Gln Gln Lys Glu Pro Met
        130                 135                 140

Ile Gly Val Asn Gln Glu Leu Ala Tyr Phe Tyr Pro Glu Leu Phe Arg
145                 150                 155                 160

Gln Phe Tyr Gln Leu Asp Ala Tyr Pro Ser Gly Ala Trp Tyr Tyr Val
                165                 170                 175

Pro Leu Gly Thr Gln Tyr Thr Asp Ala Pro Ser Phe Ser Asp Ile Pro
            180                 185                 190

Asn Pro Ile Gly Ser Glu Asn Ser Glu Lys Thr Thr Met Pro Leu Trp
        195                 200                 205

<210> SEQ ID NO 25
<211> LENGTH: 203
<212> TYPE: PRT
<213> ORGANISM: Bos taurus

<400> SEQUENCE: 25

Val Ala Leu Ala Arg Pro Lys His Pro Ile Lys His Gln Gly Leu Pro
  1               5                  10                  15

Gln Glu Val Leu Asn Glu Asn Leu Leu Arg Phe Phe Val Ala Pro Phe
             20                  25                  30

Pro Glu Val Phe Gly Lys Glu Lys Val Asn Glu Leu Ser Lys Asp Ile
```

```
                35                  40                  45
Gly Ser Glu Ser Thr Glu Asp Gln Ala Met Glu Asp Ile Lys Gln Met
 50                  55                  60

Glu Ala Glu Ser Ile Ser Ser Glu Glu Ile Val Pro Asn Ser Val
 65                  70                  75                  80

Glu Gln Lys His Ile Gln Lys Glu Asp Val Pro Ser Glu Arg Tyr Leu
                 85                  90                  95

Gly Tyr Leu Glu Gln Leu Leu Arg Leu Lys Lys Tyr Lys Val Pro Gln
                100                 105                 110

Leu Glu Ile Val Pro Asn Ser Ala Glu Glu Arg Leu His Ser Met Lys
                115                 120                 125

Glu Gly Ile His Ala Gln Gln Lys Glu Pro Met Ile Gly Val Asn Gln
                130                 135                 140

Glu Leu Ala Tyr Phe Tyr Pro Glu Leu Phe Arg Gln Phe Tyr Gln Leu
145                 150                 155                 160

Asp Ala Tyr Pro Ser Gly Ala Trp Tyr Tyr Val Pro Leu Gly Thr Gln
                165                 170                 175

Tyr Thr Asp Ala Pro Ser Phe Ser Asp Ile Pro Asn Pro Ile Gly Ser
                180                 185                 190

Glu Asn Ser Glu Lys Thr Thr Met Pro Leu Trp
                195                 200

<210> SEQ ID NO 26
<211> LENGTH: 196
<212> TYPE: PRT
<213> ORGANISM: Bos taurus

<400> SEQUENCE: 26

His Pro Ile Lys His Gln Gly Leu Pro Gln Glu Val Leu Asn Glu Asn
 1               5                  10                  15

Leu Leu Arg Phe Phe Val Ala Pro Phe Pro Glu Val Phe Gly Lys Glu
                 20                  25                  30

Lys Val Asn Glu Leu Ser Lys Asp Ile Gly Ser Glu Ser Thr Glu Asp
                 35                  40                  45

Gln Ala Met Glu Asp Ile Lys Gln Met Glu Ala Glu Ser Ile Ser Ser
 50                  55                  60

Ser Glu Glu Ile Val Pro Asn Ser Val Glu Gln Lys His Ile Gln Lys
 65                  70                  75                  80

Glu Asp Val Pro Ser Glu Arg Tyr Leu Gly Tyr Leu Glu Gln Leu Leu
                 85                  90                  95

Arg Leu Lys Lys Tyr Lys Val Pro Gln Leu Glu Ile Val Pro Asn Ser
                100                 105                 110

Ala Glu Glu Arg Leu His Ser Met Lys Glu Gly Ile His Ala Gln Gln
                115                 120                 125

Lys Glu Pro Met Ile Gly Val Asn Gln Glu Leu Ala Tyr Phe Tyr Pro
                130                 135                 140

Glu Leu Phe Arg Gln Phe Tyr Gln Leu Asp Ala Tyr Pro Ser Gly Ala
145                 150                 155                 160

Trp Tyr Tyr Val Pro Leu Gly Thr Gln Tyr Thr Asp Ala Pro Ser Phe
                165                 170                 175

Ser Asp Ile Pro Asn Pro Ile Gly Ser Glu Asn Ser Glu Lys Thr Thr
                180                 185                 190

Met Pro Leu Trp
                195
```

<210> SEQ ID NO 27
<211> LENGTH: 195
<212> TYPE: PRT
<213> ORGANISM: Bos taurus

<400> SEQUENCE: 27

```
Pro Ile Lys His Gln Gly Leu Pro Gln Glu Val Leu Asn Glu Asn Leu
1               5                   10                  15

Leu Arg Phe Phe Val Ala Pro Phe Pro Glu Val Phe Gly Lys Glu Lys
            20                  25                  30

Val Asn Glu Leu Ser Lys Asp Ile Gly Ser Glu Ser Thr Glu Asp Gln
        35                  40                  45

Ala Met Glu Asp Ile Lys Gln Met Glu Ala Glu Ser Ile Ser Ser Ser
    50                  55                  60

Glu Glu Ile Val Pro Asn Ser Val Glu Gln Lys His Ile Gln Lys Glu
65                  70                  75                  80

Asp Val Pro Ser Glu Arg Tyr Leu Gly Tyr Leu Glu Gln Leu Leu Arg
                85                  90                  95

Leu Lys Lys Tyr Lys Val Pro Gln Leu Glu Ile Val Pro Asn Ser Ala
            100                 105                 110

Glu Glu Arg Leu His Ser Met Lys Glu Gly Ile His Ala Gln Gln Lys
        115                 120                 125

Glu Pro Met Ile Gly Val Asn Gln Glu Leu Ala Tyr Phe Tyr Pro Glu
    130                 135                 140

Leu Phe Arg Gln Phe Tyr Gln Leu Asp Ala Tyr Pro Ser Gly Ala Trp
145                 150                 155                 160

Tyr Tyr Val Pro Leu Gly Thr Gln Tyr Thr Asp Ala Pro Ser Phe Ser
                165                 170                 175

Asp Ile Pro Asn Pro Ile Gly Ser Glu Asn Ser Glu Lys Thr Thr Met
            180                 185                 190

Pro Leu Trp
        195
```

<210> SEQ ID NO 28
<211> LENGTH: 174
<212> TYPE: PRT
<213> ORGANISM: Bos taurus

<400> SEQUENCE: 28

```
Ala Pro Phe Pro Glu Val Phe Gly Lys Glu Lys Val Asn Glu Leu Ser
1               5                   10                  15

Lys Asp Ile Gly Ser Glu Ser Thr Glu Asp Gln Ala Met Glu Asp Ile
            20                  25                  30

Lys Gln Met Glu Ala Glu Ser Ile Ser Ser Ser Glu Glu Ile Val Pro
        35                  40                  45

Asn Ser Val Glu Gln Lys His Ile Gln Lys Glu Asp Val Pro Ser Glu
    50                  55                  60

Arg Tyr Leu Gly Tyr Leu Glu Gln Leu Leu Arg Leu Lys Lys Tyr Lys
65                  70                  75                  80

Val Pro Gln Leu Glu Ile Val Pro Asn Ser Ala Glu Glu Arg Leu His
                85                  90                  95

Ser Met Lys Glu Gly Ile His Ala Gln Gln Lys Glu Pro Met Ile Gly
            100                 105                 110

Val Asn Gln Glu Leu Ala Tyr Phe Tyr Pro Glu Leu Phe Arg Gln Phe
        115                 120                 125
```

```
Tyr Gln Leu Asp Ala Tyr Pro Ser Gly Ala Trp Tyr Val Pro Leu
        130                 135                 140
Gly Thr Gln Tyr Thr Asp Ala Pro Ser Phe Ser Asp Ile Pro Asn Pro
145                 150                 155                 160
Ile Gly Ser Glu Asn Ser Glu Lys Thr Thr Met Pro Leu Trp
                165                 170
```

<210> SEQ ID NO 29
<211> LENGTH: 167
<212> TYPE: PRT
<213> ORGANISM: Bos taurus

<400> SEQUENCE: 29

```
Gly Lys Glu Lys Val Asn Glu Leu Ser Lys Asp Ile Gly Ser Glu Ser
1               5                   10                  15
Thr Glu Asp Gln Ala Met Glu Asp Ile Lys Gln Met Glu Ala Glu Ser
                20                  25                  30
Ile Ser Ser Ser Glu Glu Ile Val Pro Asn Ser Val Glu Gln Lys His
                35                  40                  45
Ile Gln Lys Glu Asp Val Pro Ser Glu Arg Tyr Leu Gly Tyr Leu Glu
        50                  55                  60
Gln Leu Leu Arg Leu Lys Lys Tyr Lys Val Pro Gln Leu Glu Ile Val
65                  70                  75                  80
Pro Asn Ser Ala Glu Glu Arg Leu His Ser Met Lys Glu Gly Ile His
                85                  90                  95
Ala Gln Gln Lys Glu Pro Met Ile Gly Val Asn Gln Glu Leu Ala Tyr
                100                 105                 110
Phe Tyr Pro Glu Leu Phe Arg Gln Phe Tyr Gln Leu Asp Ala Tyr Pro
            115                 120                 125
Ser Gly Ala Trp Tyr Tyr Val Pro Leu Gly Thr Gln Tyr Thr Asp Ala
        130                 135                 140
Pro Ser Phe Ser Asp Ile Pro Asn Pro Ile Gly Ser Glu Asn Ser Glu
145                 150                 155                 160
Lys Thr Thr Met Pro Leu Trp
                165
```

<210> SEQ ID NO 30
<211> LENGTH: 142
<212> TYPE: PRT
<213> ORGANISM: Bos taurus

<400> SEQUENCE: 30

```
Lys Gln Met Glu Ala Glu Ser Ile Ser Ser Ser Glu Glu Ile Val Pro
1               5                   10                  15
Asn Ser Val Glu Gln Lys His Ile Gln Lys Glu Asp Val Pro Ser Glu
                20                  25                  30
Arg Tyr Leu Gly Tyr Leu Glu Gln Leu Leu Arg Leu Lys Lys Tyr Lys
                35                  40                  45
Val Pro Gln Leu Glu Ile Val Pro Asn Ser Ala Glu Glu Arg Leu His
        50                  55                  60
Ser Met Lys Glu Gly Ile His Ala Gln Gln Lys Glu Pro Met Ile Gly
65                  70                  75                  80
Val Asn Gln Glu Leu Ala Tyr Phe Tyr Pro Glu Leu Phe Arg Gln Phe
                85                  90                  95
Tyr Gln Leu Asp Ala Tyr Pro Ser Gly Ala Trp Tyr Tyr Val Pro Leu
                100                 105                 110
```

```
Gly Thr Gln Tyr Thr Asp Ala Pro Ser Phe Ser Asp Ile Pro Asn Pro
            115                 120                 125

Ile Gly Ser Glu Asn Ser Glu Lys Thr Thr Met Pro Leu Trp
130                 135                 140
```

<210> SEQ ID NO 31
<211> LENGTH: 139
<212> TYPE: PRT
<213> ORGANISM: Bos taurus

<400> SEQUENCE: 31

```
Glu Ala Glu Ser Ile Ser Ser Glu Glu Ile Val Pro Asn Ser Val
1               5                   10                  15

Glu Gln Lys His Ile Gln Lys Glu Asp Val Pro Ser Glu Arg Tyr Leu
            20                  25                  30

Gly Tyr Leu Glu Gln Leu Leu Arg Leu Lys Lys Tyr Lys Val Pro Gln
            35                  40                  45

Leu Glu Ile Val Pro Asn Ser Ala Glu Glu Arg Leu His Ser Met Lys
50                  55                  60

Glu Gly Ile His Ala Gln Gln Lys Glu Pro Met Ile Gly Val Asn Gln
65                  70                  75                  80

Glu Leu Ala Tyr Phe Tyr Pro Glu Leu Phe Arg Gln Phe Tyr Gln Leu
                85                  90                  95

Asp Ala Tyr Pro Ser Gly Ala Trp Tyr Tyr Val Pro Leu Gly Thr Gln
            100                 105                 110

Tyr Thr Asp Ala Pro Ser Phe Ser Asp Ile Pro Asn Pro Ile Gly Ser
            115                 120                 125

Glu Asn Ser Glu Lys Thr Thr Met Pro Leu Trp
130                 135
```

<210> SEQ ID NO 32
<211> LENGTH: 137
<212> TYPE: PRT
<213> ORGANISM: Bos taurus

<400> SEQUENCE: 32

```
Glu Ser Ile Ser Ser Glu Glu Ile Val Pro Asn Ser Val Glu Gln
1               5                   10                  15

Lys His Ile Gln Lys Glu Asp Val Pro Ser Glu Arg Tyr Leu Gly Tyr
            20                  25                  30

Leu Glu Gln Leu Leu Arg Leu Lys Lys Tyr Lys Val Pro Gln Leu Glu
            35                  40                  45

Ile Val Pro Asn Ser Ala Glu Glu Arg Leu His Ser Met Lys Glu Gly
50                  55                  60

Ile His Ala Gln Gln Lys Glu Pro Met Ile Gly Val Asn Gln Glu Leu
65                  70                  75                  80

Ala Tyr Phe Tyr Pro Glu Leu Phe Arg Gln Phe Tyr Gln Leu Asp Ala
                85                  90                  95

Tyr Pro Ser Gly Ala Trp Tyr Tyr Val Pro Leu Gly Thr Gln Tyr Thr
            100                 105                 110

Asp Ala Pro Ser Phe Ser Asp Ile Pro Asn Pro Ile Gly Ser Glu Asn
            115                 120                 125

Ser Glu Lys Thr Thr Met Pro Leu Trp
130                 135
```

<210> SEQ ID NO 33
<211> LENGTH: 130

```
<212> TYPE: PRT
<213> ORGANISM: Bos taurus

<400> SEQUENCE: 33

Glu Ile Val Pro Asn Ser Val Glu Gln Lys His Ile Gln Lys Glu Asp
1               5                   10                  15

Val Pro Ser Glu Arg Tyr Leu Gly Tyr Leu Glu Gln Leu Leu Arg Leu
            20                  25                  30

Lys Lys Tyr Lys Val Pro Gln Leu Glu Ile Val Pro Asn Ser Ala Glu
        35                  40                  45

Glu Arg Leu His Ser Met Lys Glu Gly Ile His Ala Gln Gln Lys Glu
    50                  55                  60

Pro Met Ile Gly Val Asn Gln Glu Leu Ala Tyr Phe Tyr Pro Glu Leu
65                  70                  75                  80

Phe Arg Gln Phe Tyr Gln Leu Asp Ala Tyr Pro Ser Gly Ala Trp Tyr
                85                  90                  95

Tyr Val Pro Leu Gly Thr Gln Tyr Thr Asp Ala Pro Ser Phe Ser Asp
            100                 105                 110

Ile Pro Asn Pro Ile Gly Ser Glu Asn Ser Glu Lys Thr Thr Met Pro
        115                 120                 125

Leu Trp
    130

<210> SEQ ID NO 34
<211> LENGTH: 117
<212> TYPE: PRT
<213> ORGANISM: Bos taurus

<400> SEQUENCE: 34

Lys Glu Asp Val Pro Ser Glu Arg Tyr Leu Gly Tyr Leu Glu Gln Leu
1               5                   10                  15

Leu Arg Leu Lys Lys Tyr Lys Val Pro Gln Leu Glu Ile Val Pro Asn
            20                  25                  30

Ser Ala Glu Glu Arg Leu His Ser Met Lys Glu Gly Ile His Ala Gln
        35                  40                  45

Gln Lys Glu Pro Met Ile Gly Val Asn Gln Glu Leu Ala Tyr Phe Tyr
    50                  55                  60

Pro Glu Leu Phe Arg Gln Phe Tyr Gln Leu Asp Ala Tyr Pro Ser Gly
65                  70                  75                  80

Ala Trp Tyr Tyr Val Pro Leu Gly Thr Gln Tyr Thr Asp Ala Pro Ser
                85                  90                  95

Phe Ser Asp Ile Pro Asn Pro Ile Gly Ser Glu Asn Ser Glu Lys Thr
            100                 105                 110

Thr Met Pro Leu Trp
        115

<210> SEQ ID NO 35
<211> LENGTH: 111
<212> TYPE: PRT
<213> ORGANISM: Bos taurus

<400> SEQUENCE: 35

Glu Arg Tyr Leu Gly Tyr Leu Glu Gln Leu Leu Arg Leu Lys Lys Tyr
1               5                   10                  15

Lys Val Pro Gln Leu Glu Ile Val Pro Asn Ser Ala Glu Glu Arg Leu
            20                  25                  30

His Ser Met Lys Glu Gly Ile His Ala Gln Gln Lys Glu Pro Met Ile
```

-continued

```
            35                  40                  45
Gly Val Asn Gln Glu Leu Ala Tyr Phe Tyr Pro Glu Leu Phe Arg Gln
 50                  55                  60
Phe Tyr Gln Leu Asp Ala Tyr Pro Ser Gly Ala Trp Tyr Tyr Val Pro
 65                  70                  75                  80
Leu Gly Thr Gln Tyr Thr Asp Ala Pro Ser Phe Ser Asp Ile Pro Asn
                 85                  90                  95
Pro Ile Gly Ser Glu Asn Ser Glu Lys Thr Thr Met Pro Leu Trp
            100                 105                 110
```

<210> SEQ ID NO 36
<211> LENGTH: 108
<212> TYPE: PRT
<213> ORGANISM: Bos taurus

<400> SEQUENCE: 36

```
Leu Gly Tyr Leu Glu Gln Leu Arg Leu Lys Lys Tyr Lys Val Pro
 1               5                  10                  15
Gln Leu Glu Ile Val Pro Asn Ser Ala Glu Glu Arg Leu His Ser Met
                 20                  25                  30
Lys Glu Gly Ile His Ala Gln Gln Lys Glu Pro Met Ile Gly Val Asn
            35                  40                  45
Gln Glu Leu Ala Tyr Phe Tyr Pro Glu Leu Phe Arg Gln Phe Tyr Gln
 50                  55                  60
Leu Asp Ala Tyr Pro Ser Gly Ala Trp Tyr Tyr Val Pro Leu Gly Thr
 65                  70                  75                  80
Gln Tyr Thr Asp Ala Pro Ser Phe Ser Asp Ile Pro Asn Pro Ile Gly
                 85                  90                  95
Ser Glu Asn Ser Glu Lys Thr Thr Met Pro Leu Trp
            100                 105
```

<210> SEQ ID NO 37
<211> LENGTH: 104
<212> TYPE: PRT
<213> ORGANISM: Bos taurus

<400> SEQUENCE: 37

```
Glu Gln Leu Leu Arg Leu Lys Lys Tyr Lys Val Pro Gln Leu Glu Ile
 1               5                  10                  15
Val Pro Asn Ser Ala Glu Glu Arg Leu His Ser Met Lys Glu Gly Ile
                 20                  25                  30
His Ala Gln Gln Lys Glu Pro Met Ile Gly Val Asn Gln Glu Leu Ala
            35                  40                  45
Tyr Phe Tyr Pro Glu Leu Phe Arg Gln Phe Tyr Gln Leu Asp Ala Tyr
 50                  55                  60
Pro Ser Gly Ala Trp Tyr Tyr Val Pro Leu Gly Thr Gln Tyr Thr Asp
 65                  70                  75                  80
Ala Pro Ser Phe Ser Asp Ile Pro Asn Pro Ile Gly Ser Glu Asn Ser
                 85                  90                  95
Glu Lys Thr Thr Met Pro Leu Trp
            100
```

<210> SEQ ID NO 38
<211> LENGTH: 95
<212> TYPE: PRT
<213> ORGANISM: Bos taurus

<400> SEQUENCE: 38

```
Lys Val Pro Gln Leu Glu Ile Val Pro Asn Ser Ala Glu Arg Leu
1               5                   10                  15

His Ser Met Lys Glu Gly Ile His Ala Gln Gln Lys Glu Pro Met Ile
            20                  25                  30

Gly Val Asn Gln Glu Leu Ala Tyr Phe Tyr Pro Glu Leu Phe Arg Gln
            35                  40                  45

Phe Tyr Gln Leu Asp Ala Tyr Pro Ser Gly Ala Trp Tyr Tyr Val Pro
        50                  55                  60

Leu Gly Thr Gln Tyr Thr Asp Ala Pro Ser Phe Ser Asp Ile Pro Asn
65                  70                  75                  80

Pro Ile Gly Ser Glu Asn Ser Glu Lys Thr Thr Met Pro Leu Trp
                85                  90                  95

<210> SEQ ID NO 39
<211> LENGTH: 83
<212> TYPE: PRT
<213> ORGANISM: Bos taurus

<400> SEQUENCE: 39

Glu Glu Arg Leu His Ser Met Lys Gly Ile His Ala Gln Gln Lys
1               5                   10                  15

Glu Pro Met Ile Gly Val Asn Gln Glu Leu Ala Tyr Phe Tyr Pro Glu
            20                  25                  30

Leu Phe Arg Gln Phe Tyr Gln Leu Asp Ala Tyr Pro Ser Gly Ala Trp
        35                  40                  45

Tyr Tyr Val Pro Leu Gly Thr Gln Tyr Thr Asp Ala Pro Ser Phe Ser
    50                  55                  60

Asp Ile Pro Asn Pro Ile Gly Ser Glu Asn Ser Glu Lys Thr Thr Met
65                  70                  75                  80

Pro Leu Trp

<210> SEQ ID NO 40
<211> LENGTH: 79
<212> TYPE: PRT
<213> ORGANISM: Bos taurus

<400> SEQUENCE: 40

His Ser Met Lys Glu Gly Ile His Ala Gln Gln Lys Glu Pro Met Ile
1               5                   10                  15

Gly Val Asn Gln Glu Leu Ala Tyr Phe Tyr Pro Glu Leu Phe Arg Gln
            20                  25                  30

Phe Tyr Gln Leu Asp Ala Tyr Pro Ser Gly Ala Trp Tyr Tyr Val Pro
        35                  40                  45

Leu Gly Thr Gln Tyr Thr Asp Ala Pro Ser Phe Ser Asp Ile Pro Asn
    50                  55                  60

Pro Ile Gly Ser Glu Asn Ser Glu Lys Thr Thr Met Pro Leu Trp
65                  70                  75

<210> SEQ ID NO 41
<211> LENGTH: 77
<212> TYPE: PRT
<213> ORGANISM: Bos taurus

<400> SEQUENCE: 41

Met Lys Glu Gly Ile His Ala Gln Gln Lys Glu Pro Met Ile Gly Val
1               5                   10                  15

Asn Gln Glu Leu Ala Tyr Phe Tyr Pro Glu Leu Phe Arg Gln Phe Tyr
```

```
                    20                  25                  30

Gln Leu Asp Ala Tyr Pro Ser Gly Ala Trp Tyr Tyr Val Pro Leu Gly
            35                  40                  45

Thr Gln Tyr Thr Asp Ala Pro Ser Phe Ser Asp Ile Pro Asn Pro Ile
        50                  55                  60

Gly Ser Glu Asn Ser Glu Lys Thr Thr Met Pro Leu Trp
65                  70                  75

<210> SEQ ID NO 42
<211> LENGTH: 70
<212> TYPE: PRT
<213> ORGANISM: Bos taurus

<400> SEQUENCE: 42

Gln Gln Lys Glu Pro Met Ile Gly Val Asn Gln Glu Leu Ala Tyr Phe
1               5                   10                  15

Tyr Pro Glu Leu Phe Arg Gln Phe Tyr Gln Leu Asp Ala Tyr Pro Ser
            20                  25                  30

Gly Ala Trp Tyr Tyr Val Pro Leu Gly Thr Gln Tyr Thr Asp Ala Pro
        35                  40                  45

Ser Phe Ser Asp Ile Pro Asn Pro Ile Gly Ser Glu Asn Ser Glu Lys
    50                  55                  60

Thr Thr Met Pro Leu Trp
65                  70

<210> SEQ ID NO 43
<211> LENGTH: 67
<212> TYPE: PRT
<213> ORGANISM: Bos taurus

<400> SEQUENCE: 43

Glu Pro Met Ile Gly Val Asn Gln Glu Leu Ala Tyr Phe Tyr Pro Glu
1               5                   10                  15

Leu Phe Arg Gln Phe Tyr Gln Leu Asp Ala Tyr Pro Ser Gly Ala Trp
            20                  25                  30

Tyr Tyr Val Pro Leu Gly Thr Gln Tyr Thr Asp Ala Pro Ser Phe Ser
        35                  40                  45

Asp Ile Pro Asn Pro Ile Gly Ser Glu Asn Ser Glu Lys Thr Thr Met
    50                  55                  60

Pro Leu Trp
65

<210> SEQ ID NO 44
<211> LENGTH: 58
<212> TYPE: PRT
<213> ORGANISM: Bos taurus

<400> SEQUENCE: 44

Leu Ala Tyr Phe Tyr Pro Glu Leu Phe Arg Gln Phe Tyr Gln Leu Asp
1               5                   10                  15

Ala Tyr Pro Ser Gly Ala Trp Tyr Tyr Val Pro Leu Gly Thr Gln Tyr
            20                  25                  30

Thr Asp Ala Pro Ser Phe Ser Asp Ile Pro Asn Pro Ile Gly Ser Glu
        35                  40                  45

Asn Ser Glu Lys Thr Thr Met Pro Leu Trp
    50                  55

<210> SEQ ID NO 45
```

<211> LENGTH: 44
<212> TYPE: PRT
<213> ORGANISM: Bos taurus

<400> SEQUENCE: 45

Leu Asp Ala Tyr Pro Ser Gly Ala Trp Tyr Tyr Val Pro Leu Gly Thr
1               5                   10                  15

Gln Tyr Thr Asp Ala Pro Ser Phe Ser Asp Ile Pro Asn Pro Ile Gly
            20                  25                  30

Ser Glu Asn Ser Glu Lys Thr Thr Met Pro Leu Trp
        35                  40

<210> SEQ ID NO 46
<211> LENGTH: 31
<212> TYPE: PRT
<213> ORGANISM: Bos taurus

<400> SEQUENCE: 46

Leu Gly Thr Gln Tyr Thr Asp Ala Pro Ser Phe Ser Asp Ile Pro Asn
1               5                   10                  15

Pro Ile Gly Ser Glu Asn Ser Glu Lys Thr Thr Met Pro Leu Trp
            20                  25                  30

<210> SEQ ID NO 47
<211> LENGTH: 13
<212> TYPE: PRT
<213> ORGANISM: Bos taurus

<400> SEQUENCE: 47

Gly Ser Glu Asn Ser Glu Lys Thr Thr Met Pro Leu Trp
1               5                   10

<210> SEQ ID NO 48
<211> LENGTH: 97
<212> TYPE: PRT
<213> ORGANISM: Bos taurus

<400> SEQUENCE: 48

Leu Thr Cys Leu Val Ala Val Ala Leu Ala Arg Pro Lys His Pro Ile
1               5                   10                  15

Lys His Gln Gly Leu Pro Gln Glu Val Leu Asn Glu Asn Leu Leu Arg
            20                  25                  30

Phe Phe Val Ala Pro Phe Pro Glu Val Phe Gly Lys Glu Lys Val Asn
        35                  40                  45

Glu Leu Ser Lys Asp Ile Gly Ser Glu Ser Thr Glu Asp Gln Ala Met
    50                  55                  60

Glu Asp Ile Lys Gln Met Glu Ala Glu Ser Ile Ser Ser Ser Glu Glu
65                  70                  75                  80

Ile Val Pro Asn Ser Val Glu Gln Lys His Ile Gln Lys Glu Asp Val
                85                  90                  95

Pro

<210> SEQ ID NO 49
<211> LENGTH: 84
<212> TYPE: PRT
<213> ORGANISM: Bos taurus

<400> SEQUENCE: 49

Gly Ser Glu Ser Thr Glu Asp Gln Ala Met Glu Asp Ile Lys Gln Met
1               5                   10                  15

Glu Ala Glu Ser Ile Ser Ser Glu Ile Val Pro Asn Ser Val
            20                  25                  30

Glu Gln Lys His Ile Gln Lys Glu Asp Val Pro Ser Glu Arg Tyr Leu
            35                  40                  45

Gly Tyr Leu Glu Gln Leu Leu Arg Leu Lys Lys Tyr Lys Val Pro Gln
    50                  55                  60

Leu Glu Ile Val Pro Asn Ser Ala Glu Glu Arg Leu His Ser Met Lys
65                  70                  75                  80

Glu Gly Ile His

<210> SEQ ID NO 50
<211> LENGTH: 60
<212> TYPE: PRT
<213> ORGANISM: Bos taurus

<400> SEQUENCE: 50

Thr Glu Asp Gln Ala Met Glu Asp Ile Lys Gln Met Glu Ala Glu Ser
1               5                   10                  15

Ile Ser Ser Glu Glu Ile Val Pro Asn Ser Val Glu Gln Lys His
            20                  25                  30

Ile Gln Lys Glu Asp Val Pro Ser Glu Arg Tyr Leu Gly Tyr Leu Glu
            35                  40                  45

Gln Leu Leu Arg Leu Lys Lys Tyr Lys Val Pro Gln
    50                  55                  60

<210> SEQ ID NO 51
<211> LENGTH: 45
<212> TYPE: PRT
<213> ORGANISM: Bos taurus

<400> SEQUENCE: 51

Gln Met Glu Ala Glu Ser Ile Ser Ser Glu Glu Ile Val Pro Asn
1               5                   10                  15

Ser Val Glu Gln Lys His Ile Gln Lys Glu Asp Val Pro Ser Glu Arg
            20                  25                  30

Tyr Leu Gly Tyr Leu Glu Gln Leu Leu Arg Leu Lys Lys
        35                  40                  45

<210> SEQ ID NO 52
<211> LENGTH: 171
<212> TYPE: PRT
<213> ORGANISM: Bos taurus

<400> SEQUENCE: 52

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
            20                  25                  30

Glu Asn Leu Leu Arg Phe Phe Val Ala Pro Phe Pro Glu Val Phe Gly
        35                  40                  45

Lys Glu Lys Val Asn Glu Leu Ser Lys Asp Ile Gly Ser Glu Ser Thr
    50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
            100                 105                 110

```
Leu Leu Arg Leu Lys Lys Tyr Lys Val Pro Gln Leu Glu Ile Val Pro
            115                 120                 125

Asn Ser Ala Glu Glu Arg Leu His Ser Met Lys Glu Gly Ile His Ala
130                 135                 140

Gln Gln Lys Glu Pro Met Ile Gly Val Asn Gln Glu Leu Ala Tyr Phe
145                 150                 155                 160

Tyr Pro Glu Leu Phe Thr Thr Met Pro Leu Trp
                165                 170
```

<210> SEQ ID NO 53
<211> LENGTH: 200
<212> TYPE: PRT
<213> ORGANISM: Bos taurus

<400> SEQUENCE: 53

```
Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
            20                  25                  30

Glu Asn Leu Leu Arg Phe Phe Val Ala Pro Phe Pro Glu Val Phe Gly
        35                  40                  45

Lys Glu Lys Val Asn Glu Leu Ser Lys Asp Ile Gly Ser Glu Ser Thr
50                  55                  60

Glu Asp Gln Ala Met Glu Asp Ile Lys Gln Met Glu Ala Glu Ser Ile
65                  70                  75                  80

Ser Ser Ser Glu Glu Ile Val Pro Asn Ser Val Glu Gln Lys His Ile
                85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Ser Met Lys Glu Gly Ile
            115                 120                 125

His Ala Gln Gln Lys Glu Pro Met Ile Gly Val Asn Gln Glu Leu Ala
        130                 135                 140

Tyr Phe Tyr Pro Glu Leu Phe Arg Gln Phe Tyr Gln Leu Asp Ala Tyr
145                 150                 155                 160

Pro Ser Gly Ala Trp Tyr Tyr Val Pro Leu Gly Thr Gln Tyr Thr Asp
                165                 170                 175

Ala Pro Ser Phe Ser Asp Ile Pro Asn Pro Ile Gly Ser Glu Asn Ser
            180                 185                 190

Glu Lys Thr Thr Met Pro Leu Trp
        195                 200
```

<210> SEQ ID NO 54
<211> LENGTH: 222
<212> TYPE: PRT
<213> ORGANISM: Bos taurus

<400> SEQUENCE: 54

```
Met Lys Phe Phe Ile Phe Thr Cys Leu Leu Ala Val Ala Leu Ala Lys
1               5                   10                  15

Asn Thr Met Glu His Val Ser Ser Ser Glu Glu Ser Ile Ile Ser Gln
            20                  25                  30

Glu Thr Tyr Lys Gln Glu Lys Asn Met Ala Ile Asn Pro Ser Lys Glu
        35                  40                  45

Asn Leu Cys Ser Thr Phe Cys Lys Glu Val Val Arg Asn Ala Asn Glu
50                  55                  60
```

```
Glu Tyr Ser Ile Gly Ser Ser Glu Glu Ser Ala Glu Val Ala
 65                  70                  75                  80

Thr Glu Glu Val Lys Ile Thr Val Asp Asp Lys His Tyr Gln Lys Ala
                 85                  90                  95

Leu Asn Glu Ile Asn Gln Phe Tyr Gln Lys Phe Pro Gln Tyr Leu Gln
            100                 105                 110

Tyr Leu Tyr Gln Gly Pro Ile Val Leu Asn Pro Trp Asp Gln Val Lys
        115                 120                 125

Arg Asn Ala Val Pro Ile Thr Pro Thr Leu Asn Arg Glu Gln Leu Ser
    130                 135                 140

Thr Ser Glu Glu Asn Ser Lys Lys Thr Val Asp Met Glu Ser Thr Glu
145                 150                 155                 160

Val Phe Thr Lys Lys Thr Lys Leu Thr Glu Glu Lys Asn Arg Leu
                165                 170                 175

Asn Phe Leu Lys Lys Ile Ser Gln Arg Tyr Gln Lys Phe Ala Leu Pro
            180                 185                 190

Gln Tyr Leu Lys Thr Val Tyr Gln His Gln Lys Ala Met Lys Pro Trp
        195                 200                 205

Ile Gln Pro Lys Thr Lys Val Ile Pro Tyr Val Arg Tyr Leu
    210                 215                 220

<210> SEQ ID NO 55
<211> LENGTH: 199
<212> TYPE: PRT
<213> ORGANISM: Bos taurus

<400> SEQUENCE: 55

Ser Ser Glu Glu Ser Ile Ile Ser Gln Glu Thr Tyr Lys Gln Glu Lys
1               5                   10                  15

Asn Met Ala Ile Asn Pro Ser Lys Glu Asn Leu Cys Ser Thr Phe Cys
            20                  25                  30

Lys Glu Val Val Arg Asn Ala Asn Glu Glu Tyr Ser Ile Gly Ser
        35                  40                  45

Ser Ser Glu Glu Ser Ala Glu Val Ala Thr Glu Glu Val Lys Ile Thr
 50                  55                  60

Val Asp Asp Lys His Tyr Gln Lys Ala Leu Asn Glu Ile Asn Gln Phe
65                  70                  75                  80

Tyr Gln Lys Phe Pro Gln Tyr Leu Gln Tyr Leu Tyr Gln Gly Pro Ile
                85                  90                  95

Val Leu Asn Pro Trp Asp Gln Val Lys Arg Asn Ala Val Pro Ile Thr
            100                 105                 110

Pro Thr Leu Asn Arg Glu Gln Leu Ser Thr Ser Glu Glu Asn Ser Lys
        115                 120                 125

Lys Thr Val Asp Met Glu Ser Thr Glu Val Phe Thr Lys Lys Thr Lys
    130                 135                 140

Leu Thr Glu Glu Lys Asn Arg Leu Asn Phe Leu Lys Lys Ile Ser
145                 150                 155                 160

Gln Arg Tyr Gln Lys Phe Ala Leu Pro Gln Tyr Leu Lys Thr Val Tyr
                165                 170                 175

Gln His Gln Lys Ala Met Lys Pro Trp Ile Gln Pro Lys Thr Lys Val
            180                 185                 190

Ile Pro Tyr Val Arg Tyr Leu
        195
```

<210> SEQ ID NO 56
<211> LENGTH: 224
<212> TYPE: PRT
<213> ORGANISM: Bos taurus

<400> SEQUENCE: 56

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

His Pro Phe Ala Gln Thr Gln Ser Leu Val Tyr Pro Phe Pro Gly Pro
65                  70                  75                  80

Ile Pro Asn Ser Leu Pro Gln Asn Ile Pro Pro Leu Thr Gln Thr Pro
                85                  90                  95

Val Val Val Pro Pro Phe Leu Gln Pro Glu Val Met Gly Val Ser Lys
            100                 105                 110

Val Lys Glu Ala Met Ala Pro Lys His Lys Glu Met Pro Phe Pro Lys
        115                 120                 125

Tyr Pro Val Glu Pro Phe Thr Glu Ser Gln Ser Leu Thr Leu Thr Asp
    130                 135                 140

Val Glu Asn Leu His Leu Pro Leu Pro Leu Leu Gln Ser Trp Met His
145                 150                 155                 160

Gln Pro His Gln Pro Leu Pro Pro Thr Val Met Phe Pro Pro Gln Ser
                165                 170                 175

Val Leu Ser Leu Ser Gln Ser Lys Val Leu Pro Val Pro Gln Lys Ala
            180                 185                 190

Val Pro Tyr Pro Gln Arg Asp Met Pro Ile Gln Ala Phe Leu Leu Tyr
        195                 200                 205

Gln Glu Pro Val Leu Gly Pro Val Arg Gly Pro Phe Pro Ile Ile Val
    210                 215                 220

<210> SEQ ID NO 57
<211> LENGTH: 181
<212> TYPE: PRT
<213> ORGANISM: Bos taurus

<400> SEQUENCE: 57

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

His Pro Phe Ala Gln Thr Gln Ser Leu Val Tyr Pro Phe Pro Gly Pro
65                  70                  75                  80

Ile Pro Asn Ser Leu Pro Gln Asn Ile Pro Pro Leu Thr Gln Thr Pro
                85                  90                  95

Val Val Val Pro Pro Phe Leu Gln Pro Glu Val Met Gly Val Ser Lys
            100                 105                 110

Val Lys Glu Ala Met Ala Pro Lys His Lys Glu Met Pro Phe Pro Lys

```
            115                 120                 125
Tyr Pro Val Glu Pro Phe Thr Glu Ser Gln Ser Leu Thr Leu Thr Asp
    130                 135                 140

Val Glu Asn Leu His Leu Pro Leu Pro Leu Leu Gln Ser Trp Met His
145                 150                 155                 160

Gln Pro His Gln Pro Leu Pro Pro Thr Val Met Phe Pro Pro Gln Ser
                165                 170                 175

Val Leu Ser Leu Ser
            180

<210> SEQ ID NO 58
<211> LENGTH: 90
<212> TYPE: PRT
<213> ORGANISM: Bos taurus

<400> SEQUENCE: 58

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

His Pro Phe Ala Gln Thr Gln Ser Leu Val Tyr Pro Phe Pro Gly Pro
65                  70                  75                  80

Ile Pro Asn Ser Leu Pro Gln Asn Ile Pro
                85                  90

<210> SEQ ID NO 59
<211> LENGTH: 88
<212> TYPE: PRT
<213> ORGANISM: Bos taurus

<400> SEQUENCE: 59

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
        35                  40                  45

Gln Ser Glu Glu Gln Gln Gln Thr Glu Asp Glu Leu Gln Asp Lys Ile
    50                  55                  60

His Pro Phe Ala Gln Thr Gln Ser Leu Val Tyr Pro Phe Pro Gly Pro
65                  70                  75                  80

Ile Pro Asn Ser Leu Pro Gln Asn
                85

<210> SEQ ID NO 60
<211> LENGTH: 85
<212> TYPE: PRT
<213> ORGANISM: Bos taurus

<400> SEQUENCE: 60

Met Lys Val Leu Ile Leu Ala Cys Leu Val Ala Leu Ala Leu Ala Arg
1               5                   10                  15

Glu Leu Glu Glu Leu Asn Val Pro Gly Glu Ile Val Glu Ser Leu Ser
            20                  25                  30
```

```
Ser Ser Glu Glu Ser Ile Thr Arg Ile Asn Lys Lys Ile Glu Lys Phe
            35                  40                  45

Gln Ser Glu Glu Gln Gln Gln Thr Glu Asp Glu Leu Gln Asp Lys Ile
        50                  55                  60

His Pro Phe Ala Gln Thr Gln Ser Leu Val Tyr Pro Phe Pro Gly Pro
 65                  70                  75                  80

Ile Pro Asn Ser Leu
                85

<210> SEQ ID NO 61
<211> LENGTH: 84
<212> TYPE: PRT
<213> ORGANISM: Bos taurus

<400> SEQUENCE: 61

Met Lys Val Leu Ile Leu Ala Cys Leu Val Ala Leu Ala Leu Ala Arg
 1               5                  10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
            35                  40                  45

Gln Ser Glu Glu Gln Gln Gln Thr Glu Asp Glu Leu Gln Asp Lys Ile
        50                  55                  60

His Pro Phe Ala Gln Thr Gln Ser Leu Val Tyr Pro Phe Pro Gly Pro
 65                  70                  75                  80

Ile Pro Asn Ser

<210> SEQ ID NO 62
<211> LENGTH: 80
<212> TYPE: PRT
<213> ORGANISM: Bos taurus

<400> SEQUENCE: 62

Met Lys Val Leu Ile Leu Ala Cys Leu Val Ala Leu Ala Leu Ala Arg
 1               5                  10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
            35                  40                  45

Gln Ser Glu Glu Gln Gln Gln Thr Glu Asp Glu Leu Gln Asp Lys Ile
        50                  55                  60

His Pro Phe Ala Gln Thr Gln Ser Leu Val Tyr Pro Phe Pro Gly Pro
 65                  70                  75                  80

<210> SEQ ID NO 63
<211> LENGTH: 74
<212> TYPE: PRT
<213> ORGANISM: Bos taurus

<400> SEQUENCE: 63

Met Lys Val Leu Ile Leu Ala Cys Leu Val Ala Leu Ala Leu Ala Arg
 1               5                  10                  15

Glu Leu Glu Glu Leu Asn Val Pro Gly Glu Ile Val Glu Ser Leu Ser
            20                  25                  30

Ser Ser Glu Glu Ser Ile Thr Arg Ile Asn Lys Lys Ile Glu Lys Phe
            35                  40                  45

Gln Ser Glu Glu Gln Gln Gln Thr Glu Asp Glu Leu Gln Asp Lys Ile
```

```
                50                  55                  60
His Pro Phe Ala Gln Thr Gln Ser Leu Val
 65                  70

<210> SEQ ID NO 64
<211> LENGTH: 66
<212> TYPE: PRT
<213> ORGANISM: Bos taurus

<400> SEQUENCE: 64

Met Lys Val Leu Ile Leu Ala Cys Leu Val Ala Leu Ala Leu Ala Arg
 1               5                  10                  15

Glu Leu Glu Glu Leu Asn Val Pro Gly Glu Ile Val Glu Ser Leu Ser
                20                  25                  30

Ser Ser Glu Glu Ser Ile Thr Arg Ile Asn Lys Lys Ile Glu Lys Phe
            35                  40                  45

Gln Ser Glu Glu Gln Gln Gln Thr Glu Asp Glu Leu Gln Asp Lys Ile
        50                  55                  60

His Pro
 65

<210> SEQ ID NO 65
<211> LENGTH: 65
<212> TYPE: PRT
<213> ORGANISM: Bos taurus

<400> SEQUENCE: 65

Met Lys Val Leu Ile Leu Ala Cys Leu Val Ala Leu Ala Leu Ala Arg
 1               5                  10                  15

Glu Leu Glu Glu Leu Asn Val Pro Gly Glu Ile Val Glu Ser Leu Ser
                20                  25                  30

Ser Ser Glu Glu Ser Ile Thr Arg Ile Asn Lys Lys Ile Glu Lys Phe
            35                  40                  45

Gln Ser Glu Glu Gln Gln Gln Thr Glu Asp Glu Leu Gln Asp Lys Ile
        50                  55                  60

His
 65

<210> SEQ ID NO 66
<211> LENGTH: 223
<212> TYPE: PRT
<213> ORGANISM: Bos taurus

<400> SEQUENCE: 66

Lys Val Leu Ile Leu Ala Cys Leu Val Ala Leu Ala Leu Ala Arg Glu
 1               5                  10                  15

Leu Glu Glu Leu Asn Val Pro Gly Glu Ile Val Glu Ser Leu Ser Ser
                20                  25                  30

Ser Glu Glu Ser Ile Thr Arg Ile Asn Lys Lys Ile Glu Lys Phe Gln
            35                  40                  45

Ser Glu Glu Gln Gln Gln Thr Glu Asp Glu Leu Gln Asp Lys Ile His
        50                  55                  60

Pro Phe Ala Gln Thr Gln Ser Leu Val Tyr Pro Phe Pro Gly Pro Ile
 65                  70                  75                  80

Pro Asn Ser Leu Pro Gln Asn Ile Pro Pro Leu Thr Gln Thr Pro Val
                85                  90                  95

Val Val Pro Pro Phe Leu Gln Pro Glu Val Met Gly Val Ser Lys Val
            100                 105                 110
```

-continued

Lys Glu Ala Met Ala Pro Lys His Lys Glu Met Pro Phe Pro Lys Tyr
            115                 120                 125

Pro Val Glu Pro Phe Thr Glu Ser Gln Ser Leu Thr Leu Thr Asp Val
130                 135                 140

Glu Asn Leu His Leu Pro Leu Pro Leu Gln Ser Trp Met His Gln
145                 150                 155                 160

Pro His Gln Pro Leu Pro Pro Thr Val Met Phe Pro Pro Gln Ser Val
                165                 170                 175

Leu Ser Leu Ser Gln Ser Lys Val Leu Pro Val Pro Gln Lys Ala Val
                180                 185                 190

Pro Tyr Pro Gln Arg Asp Met Pro Ile Gln Ala Phe Leu Leu Tyr Gln
                195                 200                 205

Glu Pro Val Leu Gly Pro Val Arg Gly Pro Phe Pro Ile Ile Val
210                 215                 220

<210> SEQ ID NO 67
<211> LENGTH: 83
<212> TYPE: PRT
<213> ORGANISM: Bos taurus

<400> SEQUENCE: 67

Lys Val Leu Ile Leu Ala Cys Leu Val Ala Leu Ala Leu Ala Arg Glu
1               5                   10                  15

Leu Glu Glu Leu Asn Val Pro Gly Glu Ile Val Glu Ser Leu Ser Ser
                20                  25                  30

Ser Glu Glu Ser Ile Thr Arg Ile Asn Lys Lys Ile Glu Lys Phe Gln
            35                  40                  45

Ser Glu Glu Gln Gln Gln Thr Glu Asp Glu Leu Gln Asp Lys Ile His
        50                  55                  60

Pro Phe Ala Gln Thr Gln Ser Leu Val Tyr Pro Phe Pro Gly Pro Ile
65                  70                  75                  80

Pro Asn Ser

<210> SEQ ID NO 68
<211> LENGTH: 96
<212> TYPE: PRT
<213> ORGANISM: Bos taurus

<400> SEQUENCE: 68

Lys Val Leu Ile Leu Ala Cys Leu Val Ala Leu Ala Leu Ala Arg Glu
1               5                   10                  15

Leu Glu Glu Leu Asn Val Pro Gly Glu Ile Val Glu Ser Leu Ser Ser
                20                  25                  30

Ser Glu Glu Ser Ile Thr Arg Ile Asn Lys Lys Ile Glu Lys Phe Gln
            35                  40                  45

Ser Glu Glu Gln Gln Gln Thr Glu Asp Glu Leu Gln Asp Lys Ile His
        50                  55                  60

Pro Phe Ala Gln Thr Gln Ser Leu Val Tyr Pro Phe Pro Gly Pro Ile
65                  70                  75                  80

Pro Asn Ser Leu Pro Gln Asn Ile Pro Pro Leu Thr Gln Thr Pro Val
                85                  90                  95

<210> SEQ ID NO 69
<211> LENGTH: 50
<212> TYPE: PRT
<213> ORGANISM: Bos taurus

```
<400> SEQUENCE: 69

Glu Leu Asn Val Pro Gly Glu Ile Val Glu Ser Leu Ser Ser Glu
1               5                   10                  15

Glu Ser Ile Thr Arg Ile Asn Lys Lys Ile Glu Lys Phe Gln Ser Glu
            20                  25                  30

Glu Gln Gln Gln Thr Glu Asp Glu Leu Gln Asp Lys Ile His Pro Phe
        35                  40                  45

Ala Gln
    50

<210> SEQ ID NO 70
<211> LENGTH: 116
<212> TYPE: PRT
<213> ORGANISM: Bos taurus

<400> SEQUENCE: 70

Pro Gly Glu Ile Val Glu Ser Leu Ser Ser Glu Glu Ser Ile Thr
1               5                   10                  15

Arg Ile Asn Lys Lys Ile Glu Lys Phe Gln Ser Glu Glu Gln Gln Gln
            20                  25                  30

Thr Glu Asp Glu Leu Gln Asp Lys Ile His Pro Phe Ala Gln Thr Gln
        35                  40                  45

Ser Leu Val Tyr Pro Phe Pro Gly Pro Ile Pro Asn Ser Leu Pro Gln
    50                  55                  60

Asn Ile Pro Pro Leu Thr Gln Thr Pro Val Val Val Pro Pro Phe Leu
65                  70                  75                  80

Gln Pro Glu Val Met Gly Val Ser Lys Val Lys Glu Ala Met Ala Pro
                85                  90                  95

Lys His Lys Glu Met Pro Phe Pro Lys Tyr Pro Val Glu Pro Phe Thr
            100                 105                 110

Glu Ser Gln Ser
        115

<210> SEQ ID NO 71
<211> LENGTH: 50
<212> TYPE: PRT
<213> ORGANISM: Bos taurus

<400> SEQUENCE: 71

Leu Ser Ser Glu Glu Ser Ile Thr Arg Ile Asn Lys Lys Ile Glu
1               5                   10                  15

Lys Phe Gln Ser Glu Gln Gln Gln Thr Glu Asp Glu Leu Gln Asp
            20                  25                  30

Lys Ile His Pro Phe Ala Gln Thr Gln Ser Leu Val Tyr Pro Phe Pro
        35                  40                  45

Gly Pro
    50

<210> SEQ ID NO 72
<211> LENGTH: 37
<212> TYPE: PRT
<213> ORGANISM: Bos taurus

<400> SEQUENCE: 72

Lys Ile His Pro Phe Ala Gln Thr Gln Ser Leu Val Tyr Pro Phe Pro
1               5                   10                  15

Gly Pro Ile Pro Asn Ser Leu Pro Gln Asn Ile Pro Pro Leu Thr Gln
            20                  25                  30
```

```
Thr Pro Val Val Val
        35

<210> SEQ ID NO 73
<211> LENGTH: 110
<212> TYPE: PRT
<213> ORGANISM: Bos taurus

<400> SEQUENCE: 73

His Pro Phe Ala Gln Thr Gln Ser Leu Val Tyr Pro Phe Pro Gly Pro
1               5                   10                  15

Ile Pro Asn Ser Leu Pro Gln Asn Ile Pro Pro Leu Thr Gln Thr Pro
            20                  25                  30

Val Val Val Pro Pro Phe Leu Gln Pro Glu Val Met Gly Val Ser Lys
        35                  40                  45

Val Lys Glu Ala Met Ala Pro Lys His Lys Glu Met Pro Phe Pro Lys
    50                  55                  60

Tyr Pro Val Glu Pro Phe Thr Glu Ser Gln Ser Leu Thr Leu Thr Asp
65                  70                  75                  80

Val Glu Asn Leu His Leu Pro Leu Pro Leu Leu Gln Ser Trp Met His
                85                  90                  95

Gln Pro His Gln Pro Leu Pro Pro Thr Val Met Phe Pro Pro
            100                 105                 110

<210> SEQ ID NO 74
<211> LENGTH: 99
<212> TYPE: PRT
<213> ORGANISM: Bos taurus

<400> SEQUENCE: 74

Gln Ser Leu Val Tyr Pro Phe Pro Gly Pro Ile Pro Asn Ser Leu Pro
1               5                   10                  15

Gln Asn Ile Pro Pro Leu Thr Gln Thr Pro Val Val Val Pro Pro Phe
            20                  25                  30

Leu Gln Pro Glu Val Met Gly Val Ser Lys Val Lys Glu Ala Met Ala
        35                  40                  45

Pro Lys His Lys Glu Met Pro Phe Pro Lys Tyr Pro Val Glu Pro Phe
    50                  55                  60

Thr Glu Ser Gln Ser Leu Thr Leu Thr Asp Val Glu Asn Leu His Leu
65                  70                  75                  80

Pro Leu Pro Leu Leu Gln Ser Trp Met His Gln Pro His Gln Pro Leu
                85                  90                  95

Pro Pro Thr

<210> SEQ ID NO 75
<211> LENGTH: 77
<212> TYPE: PRT
<213> ORGANISM: Bos taurus

<400> SEQUENCE: 75

Pro Pro Phe Leu Gln Pro Glu Val Met Gly Val Ser Lys Val Lys Glu
1               5                   10                  15

Ala Met Ala Pro Lys His Lys Glu Met Pro Phe Pro Lys Tyr Pro Val
            20                  25                  30

Glu Pro Phe Thr Glu Ser Gln Ser Leu Thr Leu Thr Asp Val Glu Asn
        35                  40                  45

Leu His Leu Pro Leu Pro Leu Leu Gln Ser Trp Met His Gln Pro His
```

```
                50                  55                  60
Gln Pro Leu Pro Pro Thr Val Met Phe Pro Pro Gln Ser
 65                  70                  75

<210> SEQ ID NO 76
<211> LENGTH: 64
<212> TYPE: PRT
<213> ORGANISM: Bos taurus

<400> SEQUENCE: 76

Pro Pro Phe Leu Gln Pro Glu Val Met Gly Val Ser Lys Val Lys Glu
  1               5                  10                  15

Ala Met Ala Pro Lys His Lys Glu Met Pro Phe Pro Lys Tyr Pro Val
             20                  25                  30

Glu Pro Phe Thr Glu Ser Gln Ser Leu Thr Leu Thr Asp Val Glu Asn
         35                  40                  45

Leu His Leu Pro Leu Pro Leu Leu Gln Ser Trp Met His Gln Pro His
     50                  55                  60

<210> SEQ ID NO 77
<211> LENGTH: 190
<212> TYPE: PRT
<213> ORGANISM: Bos taurus

<400> SEQUENCE: 77

Met Met Lys Ser Phe Phe Leu Val Val Thr Ile Leu Ala Leu Thr Leu
  1               5                  10                  15

Pro Phe Leu Gly Ala Gln Glu Gln Asn Gln Glu Gln Pro Ile Arg Cys
             20                  25                  30

Glu Lys Asp Glu Arg Phe Phe Ser Asp Lys Ile Ala Lys Tyr Ile Pro
         35                  40                  45

Ile Gln Tyr Val Leu Ser Arg Tyr Pro Ser Tyr Gly Leu Asn Tyr Tyr
     50                  55                  60

Gln Gln Lys Pro Val Ala Leu Ile Asn Asn Gln Phe Leu Pro Tyr Pro
 65                  70                  75                  80

Tyr Tyr Ala Lys Pro Ala Ala Val Arg Ser Pro Ala Gln Ile Leu Gln
                 85                  90                  95

Trp Gln Val Leu Ser Asn Thr Val Pro Ala Lys Ser Cys Gln Ala Gln
            100                 105                 110

Pro Thr Thr Met Ala Arg His Pro His Pro His Leu Ser Phe Met Ala
        115                 120                 125

Ile Pro Pro Lys Lys Asn Gln Asp Lys Thr Glu Ile Pro Thr Ile Asn
    130                 135                 140

Thr Ile Ala Ser Gly Glu Pro Thr Ser Thr Pro Thr Ile Glu Ala Val
145                 150                 155                 160

Glu Ser Thr Val Ser Thr Leu Glu Ala Ser Pro Glu Val Ile Glu Ser
                165                 170                 175

Pro Pro Glu Ile Asn Thr Val Gln Val Thr Ser Thr Ala Val
            180                 185                 190

<210> SEQ ID NO 78
<211> LENGTH: 120
<212> TYPE: PRT
<213> ORGANISM: Bos taurus

<400> SEQUENCE: 78

Met Met Lys Ser Phe Phe Leu Val Val Thr Ile Leu Ala Leu Thr Leu
  1               5                  10                  15
```

Pro Phe Leu Gly Ala Gln Glu Gln Asn Gln Glu Gln Pro Ile Arg Cys
            20                  25                  30

Glu Lys Asp Glu Arg Phe Phe Ser Asp Lys Ile Ala Lys Tyr Ile Pro
         35                  40                  45

Ile Gln Tyr Val Leu Ser Arg Tyr Pro Ser Tyr Gly Leu Asn Tyr Tyr
 50                  55                  60

Gln Gln Lys Pro Val Ala Leu Ile Asn Asn Gln Phe Leu Pro Tyr Pro
 65                  70                  75                  80

Tyr Tyr Ala Lys Pro Ala Ala Val Arg Ser Pro Ala Gln Ile Leu Gln
             85                  90                  95

Trp Gln Val Leu Ser Asn Thr Val Pro Ala Lys Ser Cys Gln Ala Gln
            100                 105                 110

Pro Thr Thr Met Ala Arg His Pro
            115                 120

<210> SEQ ID NO 79
<211> LENGTH: 93
<212> TYPE: PRT
<213> ORGANISM: Bos taurus

<400> SEQUENCE: 79

Met Lys Ser Phe Phe Leu Val Val Thr Ile Leu Ala Leu Thr Leu Pro
 1               5                  10                  15

Phe Leu Gly Ala Gln Glu Gln Asn Gln Glu Gln Pro Ile Arg Cys Glu
             20                  25                  30

Lys Asp Glu Arg Phe Phe Ser Asp Lys Ile Ala Lys Tyr Ile Pro Ile
         35                  40                  45

Gln Tyr Val Leu Ser Arg Tyr Pro Ser Tyr Gly Leu Asn Tyr Tyr Gln
 50                  55                  60

Gln Lys Pro Val Ala Leu Ile Asn Asn Gln Phe Leu Pro Tyr Pro Tyr
 65                  70                  75                  80

Tyr Ala Lys Pro Ala Ala Val Arg Ser Pro Ala Gln Ile
             85                  90

<210> SEQ ID NO 80
<211> LENGTH: 60
<212> TYPE: PRT
<213> ORGANISM: Bos taurus

<400> SEQUENCE: 80

Pro Lys Lys Asn Gln Asp Lys Thr Glu Ile Pro Thr Ile Asn Thr Ile
 1               5                  10                  15

Ala Ser Gly Glu Pro Thr Ser Thr Pro Thr Ile Glu Ala Val Glu Ser
             20                  25                  30

Thr Val Ser Thr Leu Glu Ala Ser Pro Glu Val Ile Glu Ser Pro Pro
         35                  40                  45

Glu Ile Asn Thr Val Gln Val Thr Ser Thr Ala Val
 50                  55                  60

<210> SEQ ID NO 81
<211> LENGTH: 38
<212> TYPE: PRT
<213> ORGANISM: Bos taurus

<400> SEQUENCE: 81

Ser Thr Pro Thr Ile Glu Ala Val Glu Ser Thr Val Ser Thr Leu Glu
 1               5                  10                  15

Ala Ser Pro Glu Val Ile Glu Ser Pro Glu Ile Asn Thr Val Gln
         20                  25                  30

Val Thr Ser Thr Ala Val
         35

<210> SEQ ID NO 82
<211> LENGTH: 141
<212> TYPE: PRT
<213> ORGANISM: Bos taurus

<400> SEQUENCE: 82

Met Ser Phe Val Ser Leu Leu Val Gly Ile Leu Phe His Ala Thr
1               5                   10                  15

Gln Ala Glu Gln Leu Thr Lys Cys Glu Val Phe Arg Glu Leu Lys Asp
                 20                  25                  30

Leu Lys Gly Tyr Gly Gly Val Ser Leu Pro Glu Trp Val Cys Thr Thr
         35                  40                  45

Phe His Thr Ser Gly Tyr Asp Thr Gln Ala Ile Val Gln Asn Asn Asp
     50                  55                  60

Ser Thr Glu Tyr Gly Leu Phe Gln Ile Asn Asn Lys Ile Trp Cys Lys
65               70                  75                  80

Asp Asp Gln Asn Pro His Ser Ser Asn Ile Cys Asn Ile Ser Cys Asp
                 85                  90                  95

Lys Phe Leu Asp Asp Asp Leu Thr Asp Asp Ile Met Cys Val Lys Lys
            100                 105                 110

Ile Leu Asp Lys Val Gly Ile Asn Tyr Trp Leu Ala His Lys Ala Leu
        115                 120                 125

Cys Ser Glu Lys Leu Asp Gln Trp Leu Cys Glu Lys Leu
    130                 135                 140

<210> SEQ ID NO 83
<211> LENGTH: 606
<212> TYPE: PRT
<213> ORGANISM: Bos taurus

<400> SEQUENCE: 83

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
                 20                  25                  30

His Arg Phe Lys Asp Leu Gly Glu Glu His Phe Lys Gly Leu Val Leu
         35                  40                  45

Ile Ala Phe Ser Gln Tyr Leu Gln Gln Cys Pro Phe Asp Glu His Val
     50                  55                  60

Lys Leu Val Asn Glu Leu Glu Phe Ala Lys Thr Cys Val Ala Asp Glu
65               70                  75                  80

Ser His Ala Gly Cys Glu Lys Ser Leu His Thr Leu Phe Gly Asp Glu
                 85                  90                  95

Leu Cys Lys Val Ala Ser Leu Arg Glu Thr Tyr Gly Asp Met Ala Asp
            100                 105                 110

Cys Cys Glu Lys Gln Glu Pro Glu Arg Asn Glu Cys Phe Leu Ser His
        115                 120                 125

Lys Asp Asp Ser Pro Asp Leu Pro Lys Leu Lys Pro Asp Pro Asn Thr
    130                 135                 140

Leu Cys Asp Glu Phe Lys Ala Asp Glu Lys Lys Phe Trp Gly Lys Tyr
145                 150                 155                 160

-continued

```
Leu Tyr Glu Ile Ala Arg Arg His Pro Tyr Phe Tyr Ala Pro Glu Leu
            165                 170                 175

Leu Tyr Tyr Ala Asn Lys Tyr Asn Gly Val Phe Gln Glu Cys Cys Gln
        180                 185                 190

Ala Glu Asp Lys Gly Ala Cys Leu Leu Pro Lys Ile Glu Thr Met Arg
    195                 200                 205

Glu Lys Val Leu Thr Ser Ser Ala Arg Gln Arg Leu Arg Cys Ala Ser
210                 215                 220

Ile Gln Lys Phe Gly Glu Arg Ala Leu Lys Ala Trp Ser Val Ala Arg
225                 230                 235                 240

Leu Ser Gln Lys Phe Pro Lys Ala Glu Phe Val Glu Val Thr Lys Leu
                245                 250                 255

Val Thr Asp Leu Thr Lys Val His Lys Glu Cys Cys His Gly Asp Leu
            260                 265                 270

Leu Glu Cys Ala Asp Asp Arg Ala Asp Leu Ala Lys Tyr Ile Cys Asp
        275                 280                 285

Asn Gln Asp Thr Ile Ser Ser Lys Leu Lys Glu Cys Cys Asp Lys Pro
    290                 295                 300

Leu Leu Glu Lys Ser His Cys Ile Ala Glu Val Glu Lys Asp Ala Ile
305                 310                 315                 320

Pro Glu Asn Leu Pro Pro Leu Thr Ala Asp Phe Ala Glu Asp Lys Asp
                325                 330                 335

Val Cys Lys Asn Tyr Gln Glu Ala Lys Asp Ala Phe Leu Gly Ser Phe
            340                 345                 350

Leu Tyr Glu Tyr Ser Arg Arg His Pro Glu Tyr Ala Val Ser Val Leu
        355                 360                 365

Leu Arg Leu Ala Lys Glu Tyr Glu Ala Thr Leu Glu Glu Cys Cys Ala
    370                 375                 380

Lys Asp Asp Pro His Ala Cys Tyr Ser Thr Val Phe Asp Leu Leu Lys
385                 390                 395                 400

His Leu Val Asp Glu Pro Gln Asn Leu Ile Lys Gln Asn Cys Asp Gln
                405                 410                 415

Phe Glu Lys Leu Gly Glu Tyr Gly Phe Gln Asn Ala Leu Ile Val Arg
            420                 425                 430

Tyr Thr Arg Lys Val Pro Gln Val Ser Thr Pro Thr Leu Val Glu Val
        435                 440                 445

Ser Arg Ser Leu Gly Lys Val Gly Thr Arg Cys Cys Thr Lys Pro Glu
    450                 455                 460

Ser Glu Arg Met Pro Cys Thr Glu Asp Tyr Leu Ser Leu Ile Leu Asn
465                 470                 475                 480

Arg Leu Cys Val Leu His Glu Lys Thr Pro Val Ser Glu Lys Val Thr
                485                 490                 495

Lys Cys Cys Thr Glu Ser Leu Val Asn Arg Arg Pro Cys Phe Ser Ala
            500                 505                 510

Leu Thr Pro Asp Glu Thr Tyr Val Pro Lys Ala Phe Asp Glu Lys Leu
        515                 520                 525

Phe Thr Phe His Ala Asp Ile Cys Thr Leu Pro Asp Thr Glu Lys Gln
    530                 535                 540

Ile Lys Lys Gln Thr Ala Leu Val Glu Leu Leu Lys His Lys Pro Lys
545                 550                 555                 560

Ala Thr Glu Glu Gln Leu Lys Thr Val Met Glu Asn Phe Val Ala Phe
                565                 570                 575

Val Asp Lys Cys Cys Ala Ala Asp Asp Lys Glu Ala Cys Phe Ala Val
```

```
                        580                 585                 590
Glu Gly Pro Lys Leu Val Val Ser Thr Gln Thr Ala Leu Ala
            595                 600                 605

<210> SEQ ID NO 84
<211> LENGTH: 709
<212> TYPE: PRT
<213> ORGANISM: Bos taurus

<400> SEQUENCE: 84

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
    50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
    130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Ser Val Asp Gly Lys Glu Asp Leu Ile Trp
        275                 280                 285

Lys Leu Leu Ser Lys Ala Gln Glu Lys Phe Gly Lys Asn Lys Ser Arg
    290                 295                 300

Ser Phe Gln Leu Phe Gly Ser Pro Pro Gly Gln Arg Asp Leu Leu Phe
305                 310                 315                 320

Lys Asp Ser Ala Leu Gly Phe Leu Arg Ile Pro Ser Lys Val Asp Ser
                325                 330                 335

Ala Leu Tyr Leu Gly Ser Arg Tyr Leu Thr Thr Leu Lys Asn Leu Arg
            340                 345                 350
```

```
Glu Thr Ala Glu Val Lys Ala Arg Tyr Thr Arg Val Val Trp Cys
    355                 360                 365
Ala Val Gly Pro Glu Glu Gln Lys Lys Cys Gln Gln Trp Ser Gln Gln
    370                 375                 380
Ser Gly Gln Asn Val Thr Cys Ala Thr Ala Ser Thr Thr Asp Asp Cys
385                 390                 395                 400
Ile Val Leu Val Leu Lys Gly Glu Ala Asp Ala Leu Asn Leu Asp Gly
                405                 410                 415
Gly Tyr Ile Tyr Thr Ala Gly Lys Cys Gly Leu Val Pro Val Leu Ala
                420                 425                 430
Glu Asn Arg Lys Ser Ser Lys His Ser Ser Leu Asp Cys Val Leu Arg
    435                 440                 445
Pro Thr Glu Gly Tyr Leu Ala Val Ala Val Lys Lys Ala Asn Glu
    450                 455                 460
Gly Leu Thr Trp Asn Ser Leu Lys Asp Lys Ser Cys His Thr Ala
465                 470                 475                 480
Val Asp Arg Thr Ala Gly Trp Asn Ile Pro Met Gly Leu Ile Val Asn
                485                 490                 495
Gln Thr Gly Ser Cys Ala Phe Asp Glu Phe Phe Ser Gln Ser Cys Ala
                500                 505                 510
Pro Gly Ala Asp Pro Lys Ser Arg Leu Cys Ala Leu Cys Ala Gly Asp
                515                 520                 525
Asp Gln Gly Leu Asp Lys Cys Val Pro Asn Ser Lys Glu Lys Tyr Tyr
    530                 535                 540
Gly Tyr Thr Gly Ala Phe Arg Cys Leu Ala Glu Asp Val Gly Asp Val
545                 550                 555                 560
Ala Phe Val Lys Asn Asp Thr Val Trp Glu Asn Thr Asn Gly Glu Ser
                565                 570                 575
Thr Ala Asp Trp Ala Lys Asn Leu Asn Arg Glu Asp Phe Arg Leu Leu
                580                 585                 590
Cys Leu Asp Gly Thr Arg Lys Pro Val Thr Glu Ala Gln Ser Cys His
    595                 600                 605
Leu Ala Val Ala Pro Asn His Ala Val Val Ser Arg Ser Asp Arg Ala
    610                 615                 620
Ala His Val Lys Gln Val Leu Leu His Gln Ala Leu Phe Gly Lys
625                 630                 635                 640
Asn Gly Lys Asn Cys Pro Asp Lys Phe Cys Leu Phe Lys Ser Glu Thr
                645                 650                 655
Lys Asn Leu Leu Phe Asn Asp Asn Thr Glu Cys Leu Ala Lys Leu Gly
                660                 665                 670
Gly Arg Pro Thr Tyr Glu Glu Tyr Leu Gly Thr Glu Tyr Val Thr Ala
    675                 680                 685
Ile Ala Asn Leu Lys Lys Cys Ser Thr Ser Pro Leu Leu Glu Ala Cys
    690                 695                 700
Ala Phe Leu Thr Arg
705
```

METHOD FOR IDENTIFYING ALLERGENIC PROTEINS AND PEPTIDES

RELATED APPLICATION

This application claims priority from and benefit of U.S. Provisional Patent Application Ser. No. 61/196,416, entitled Method For Identifying Allergenic Proteins And Peptides, filed Oct. 17, 2008, the disclosure of which is hereby incorporated by reference herein in its entirety.

TECHNICAL FIELD

The present disclosure relates to a method for identifying allergenic proteins and peptides. More specifically, the present disclosure provides a method for identifying allergenic milk proteins and/or peptides comprising the steps of: providing at least one expression library comprising DNA or cDNA derived from the mammary gland tissue of a lactating cow, expressing at least one protein or peptide encoded by said expression library, determining the binding capacity of said at least one protein or peptide to IgE of at least one serum of an individual who is sensitive to cow's milk, contacting the at least one protein or peptide exhibiting an IgE binding capacity as determined with basophil cells, eosinophil cells or mast cells and identifying the at least one protein or peptide as being allergenic when said basophil cells, eosinophil cells or mast cells release at least one mediator upon contact with said at least one protein or peptide.

BACKGROUND OF THE DISCLOSURE

Approximately 2-8% of infants younger than 3 years and about 2% of the adult population are affected by food hypersensitivities. About 80% of allergic reactions in children are the result of hypersensitivity to cow's milk (CM), hen's egg and legumes (e.g. peanuts and soybeans). In the adult population, however, allergy to fruits, peanuts and tree nuts represent the hypersensitivities with the highest prevalence.

Cow's milk is among the first foods introduced into an infant's diet and thus one of the most common causes of food allergy in young children. About 2.5% of neonates show adverse reactions to cow's milk in the first year of their life.

Symptoms of cow's milk allergy (CMA) are either of immediate or delayed type and they range from mild to severe reactions that involve the skin, the respiratory tract, gastrointestinal tract and in the worst case appear as life-threatening systemic reactions (anaphylaxis). In contrast to the cell-mediated delayed type reactions, immediate reactions are caused by the production of immunoglobulin E (IgE) antibodies in response to otherwise harmless antigens (Type I hypersensitivity). The interaction of IgE antibodies with the allergenic molecule leads to specific activation of effector cells (mast cells, basophil granulocytes) and to a subsequent release of inflammatory mediators like histamine, prostaglandine, and leukotriene which are responsible for the immediate-type allergic reactions.

Cow's milk contains more than 25 proteins and some of them are known to be allergenic. By the action of chymosin (rennin) or by acidification of milk to pH 4.6 two fractions are obtained: Twenty percent of the proteins are found in the whey fraction and 80% of proteins comprise the casein fraction. Allergenic molecules are contained in both fractions and considered either major or minor allergens depending on the incidence of documented allergic responses in the CMA population.

Major allergens present in cow's milk are alpha-lactalbumin, beta-lactoglobulin, alphaS1-casein, beta-casein and kappa-casein. Minor allergens present in cow's milk are alphaS2-casein, lactoferrin, bovine serum albumin and immunoglobulin.

Alpha-lactalbumin (Bos d 4), beta-lactoglobulin (Bos d 5), immunoglobulins (Bos d 7), BSA and lactoferrin are the well-known IgE-reactive components in whey. AlphaS1-casein, alphaS2-casein, beta-casein and kappa-casein are the potent allergens in the casein fraction (Bos d 8) (Wal, 2004).

In the whey fraction beta-lactoglobulin (BLG) and alpha-lactalbumin (ALA) are regarded as major allergens. Beta-lactoglobulin is a globular and very stable protein which belongs to the lipocalins, a protein superfamily, that bind hydrophobic ligands. Other allergens, like the major dog allergens Can f 1 and Can f 2 and allergens of other furred animals (horse, cat, and guinea pig) also belong to this protein superfamily. Beta-lactoglobulin naturally occurs in a dimeric form with a molecular weight of 36 kDa. There are two major isoforms of beta-lactoglobulin, the genetic variants A (BLGA) and B (BLGB), which differ in amino acids 64 and 118 (aspartic acid and valine in BLGA, glycine and alanine in BLGB). Stability and the fact that beta-lactoglobulin belongs to the family of lipocalins may explain the high allergenic potential of this molecule.

Alpha-lactalbumin is a 14 kDa acidic $Ca^{2+}$ binding monomer stabilized by four disulfide bridges. It is a regulatory component in the galactosyltransferase system that synthesizes lactose. Sequence analysis showed high amino acid sequence homology to human alpha-lactalbumin (hALA) and lysozyme from hen's egg; a major allergen of hen's egg. The allergenicity of alpha-lactalbumin may be explained by its stability.

In suspension the proteins of the casein fraction form ordered aggregates (micelles) with a constant proportion of the individual molecules: alphaS1- and alphaS2-casein 37% each, beta- and kappa-casein 13% each. The four casein molecules have little primary structure homology, have different functional properties, but are all phosphorylated proteins with rheomorph, highly hydrated tertiary structures that can be easily degraded by some proteases. This sensitivity to proteolytic digestion is a rather unusual characteristic for an important allergen. Cow's milk caseins share amino acid sequence homologies of up to 90% with caseins of other mammals, like goat and sheep. This sequence homology might be the reason for the frequently observed cross-reactivity between cow's milk and milk from other animals.

The present disclosure addresses the need to provide methods which allow to identify allergenic proteins and peptides present in a biological source. The present disclosure thereby also addresses the need to provide methods which allow one to identify non-allergenic proteins and peptides present in a biological source, in particular in cow milk and nutritional formulations containing cow milk. Moreover, the disclosure provides methods for diagnosing and treating an allergy in an individual.

SUMMARY OF THE DISCLOSURE

An embodiment of the present disclosure relates to a method for identifying allergenic milk proteins and peptides, which comprises the steps of providing at least one expression library comprising DNA or cDNA derived from the mammary gland tissue of a lactating cow, expressing at least one protein or peptide encoded by said expression library, determining the binding capacity of said at least one protein or peptide to IgE of at least one serum of an individual who is sensitive to cow's milk, contacting the said at least one protein or peptide exhibiting an IgE binding capacity with basophil cells, eosinophil cells or mast cells, and identifying the said at least one protein or peptide as being allergenic when said basophil cells, eosinophil cells or mast cells release at least one mediator upon contact with said at least one protein or peptide. Thus, the disclosure in another embodiment provides a method for identifying at least one allergenic milk protein or peptide, which comprises the steps of providing at least one expression library comprising DNA or cDNA derived from the mammary gland tissue of a lactating cow, expressing at least one protein or peptide encoded by said expression library, determining the binding capacity of said at least one protein or peptide to IgE of at least one serum of an individual who is sensitive to cow's milk, contacting the said at least one protein or peptide exhibiting an IgE binding capacity with basophil cells, eosinophil cells or mast cells, and identifying the at least one protein or peptide as being allergenic when said basophil cells, eosinophil cells or mast cells release at least one mediator upon contact with said at least one protein or peptide. In even other words the disclosure relates to the method as described in paragraph [0012], wherein the allergenic proteins and peptides are milk allergenic proteins and peptides, the at least one expression library comprises DNA or cDNA derived from the mammary gland tissue of a lactating cow, and the individual who is sensitive to the allergenic source is an individual who is sensitive to cow milk.

According to a further embodiment the disclosed methods can further comprise a step of determining the amino acid sequence of the at least one protein or peptide identified by the methods.

The present disclosure also provides a method for identifying allergenic proteins and/or peptides encoded by a DNA or cDNA expression library comprising the steps of providing at least one expression library comprising DNA or cDNA derived from at least one allergen source, expressing at least one protein or peptide encoded by said expression library, determining the binding capacity of said at least one protein or peptide to IgE of at least one serum of an individual who is sensitive to the at least one allergen source, in particular cow milk and nutritional formulations containing cow milk, contacting the said at least one protein or peptide exhibiting an IgE binding capacity with basophil cells, eosinophil cells or mast cells, and identifying the at least one protein or peptide as being allergenic when said basophil cells, eosinophil cells or mast cells release at least one mediator upon contact with said at least one protein or peptide. Thus, the disclosure provides a method for identifying at least one allergenic protein or peptide encoded by a DNA or cDNA expression library comprising the steps of providing at least one expression library comprising DNA or cDNA derived from at least one allergen source, expressing at least one protein or peptide encoded by said expression library, determining the binding capacity of said at least one protein or peptide to IgE of at least one serum of an individual who is sensitive to the at least one allergen source, contacting the said at least one protein or peptide exhibiting an IgE binding capacity with basophil cells eosinophil cells or mast cells, and identifying the at least one protein or peptide as being allergenic when said basophil cells, eosinophil cells or mast cells release at least one mediator upon contact with said at least one protein or peptide.

A further embodiment relates to a method for detecting allergenic proteins and peptides in a cow milk comprising sample comprising the step of determining the presence of at least one protein or peptide from FIGS. 1A, 1B and 1C (SEQ ID Nos. 22-84) and Table 1A, 1B and Table 2 (SEQ ID Nos. 1-21).

According to this embodiment of the disclosure, the cow milk can be a hydrolysed cow milk. Furthermore, said presence of at least one protein or peptide can be determined by mass spectrometry. Preferably, the proteins and peptides present in the sample are isolated prior to mass spectrometry. Proteins and peptides can be isolated by an electrophoretic method or by high performance liquid chromatography. Preferably, the electrophoretic method can be two-dimensional electrophoresis.

Another embodiment of the disclosure relates to a protein or peptide identified by the method. A further embodiment relates to or a protein or peptide selected from FIGS. 1A, 1B, 1C (SEQ ID Nos 22-84), Tables 1A, 1B, or Table 2 (SEQ ID Nos. 1-21).

A further embodiment relates to at least one protein or peptide for use in the diagnosis of an allergy or a predisposition for an allergy in an individual. It is preferred that the allergy is a milk allergy.

A different embodiment of the disclosure refers to a method of diagnosing an allergy or a predisposition for an allergy in an individual comprising administering at least one protein or peptide as mentioned herein to an individual suspected of being allergic or becoming allergic and assessing whether the individual developed an allergic reaction against the protein or peptide.

According to this embodiment, it is preferred that the allergy or the predisposition for an allergy is a milk allergy or a predisposition for a milk allergy. The method of this embodiment preferably comprises additionally a skin test and/or a blood test. The skin test is preferably selected from (i) a skin prick test, (ii) an intradermal test, (iii) a skin patch test, or (iv) any combination of tests of (i) to (iii), wherein a positive result of the tests (i) to (iv) is indicative of an allergy or a predisposition for an allergy in an individual. The blood test preferably comprises the steps of (i) contacting at least one protein or peptide with a blood sample, serum sample or plasma sample from said individual, and (ii) determining if said at least one protein or peptide binds to an IgE antibody in said blood sample, serum sample or plasma sample, wherein binding of said at least one protein or peptide to an IgE antibody is indicative of an allergy or a predisposition of an allergy in said individual; and/or (i') contacting at least one protein or peptide with basophil cells, eosinophil cells or mast cells of said individual, and (ii') determining if said basophil cells, eosinophil cells or mast cells release upon contact with the at least one protein or peptide at least one mediator, or degranulate upon contact with the at least one protein or peptide, wherein release of said at least one mediator upon contact with said at least one protein or peptide or degranulation upon contact with said at least one protein or peptide is indicative of an allergy or a predisposition for an allergy in said individual.

Another embodiment of the disclosure refers to at least one protein or peptide for use in an allergen-immunotherapy of an allergy in an individual. It is preferred that the allergy is a milk allergy.

In a further embodiment the disclosure relates to a method of allergen-immunotherapy for an allergy in an individual comprising administering at least one protein or peptide of the disclosure. It is preferred that the allergy is a milk allergy.

In another embodiment the disclosure relates to a method for determining an allergy or a predisposition for an allergy in an individual, the method comprising a) contacting at least one protein or peptide of the disclosure with a blood sample, serum sample or plasma sample, wherein said blood sample, serum sample or plasma sample is isolated from said individual, and b) determining if said at least one protein or peptide binds to an IgE antibody in said blood sample, serum sample or plasma sample, wherein binding of said at east one protein or peptide to an IgE antibody is indicative for an allergy or a predisposition for an allergy in said individual; and/or a') contacting at least one protein or peptide of the disclosure with basophil cells, eosinophil cells or mast cells wherein said basophil cells, eosinophil cells or mast cells have been isolated from said individual, and b') determining if said basophil cells, eosinophil cells or mast cells (i) release upon contact with the at least one protein or peptide at least one mediator, or (ii) degranulate upon contact with the at least one protein or peptide, wherein release of said at least one mediator upon contact with said at least one protein or peptide or degranulation upon contact with said at least one protein or peptide is indicative for an allergy or a predisposition for an allergy in said individual.

According to this embodiment, it is preferred that the allergy or the predisposition for an allergy is a milk allergy or the predisposition for a milk allergy. Preferably the method according to this embodiment further comprises discriminating individuals with a severe allergy from individuals which are sensitized but asymptomatic, and/or discriminating individuals who grow out of an allergy from individuals who do not grow out of an allergy.

In a further embodiment the disclosure refers to a method for identifying a IgE-reactive non-allergenic milk protein or peptide encoded by a DNA or cDNA of at least one expression library comprising the steps of: a) providing at least one expression library comprising DNA or cDNA derived from the mammary gland tissue of a lactating cow, b) expressing at least one protein or peptide encoded by said expression library, c) determining the binding capacity of said at least one protein or peptide to IgE of at least one serum of an individual who is sensitive to cow's milk, d) contacting the at least one protein or peptide exhibiting an IgE binding capacity as determined in step c) with basophil cells, eosinophil cells or mast cells and e) determining if said basophil cells, eosinophil cells or mast cells (i) release upon contact with the at least one protein or peptide at least one mediator, or (ii) degranulate upon contact with the at least one protein or peptide, wherein release of the at least one mediator upon contact with the at least one protein or peptide or degranulation upon contact with the at least one protein or peptide is indicative for an allergy or a predisposition for an allergy in said individual.

According to this embodiment, the at least one protein or peptide identified by the method or specifically disclosed herein is for use in treating an allergy. Also provided in accordance with the present disclosure is a method of treating an allergy in an individual comprising administering at least one protein or peptide identified by the method or specifically disclosed herein.

It is preferred in all applicable embodiments of the disclosure that said individual or patient is a human. The eosinophil cells, mast cells or basophil cells are as a rule mammalian and may be of human origin.

BRIEF DESCRIPTION OF THE DRAWINGS

FIG. 1B shows the deduced amino acid sequences of cDNAs encoding IgE-reactive full-length beta-, kappa-casein and beta-lactoglobulin and IgE-reactive fragments of these proteins.

The amino acid sequence of full-length beta-, kappa-casein and beta-lactoglobulin are shown at the top. The sequence of IgE-reactive fragments (clone numbers right margin) are displayed as lines. The numbers indicate the first and last amino acid of each clone. Underlined sequences in the beta-casein sequence (top) correspond to non-allergenic peptides identified by mass spectrometric analysis of an extensively hydrolysed hypoallergenic milk formula.

FIG. 1C shows amino acid sequences of alpha-lactalbumin, bovine serum albumin and lactoferrin.

Figure 2:
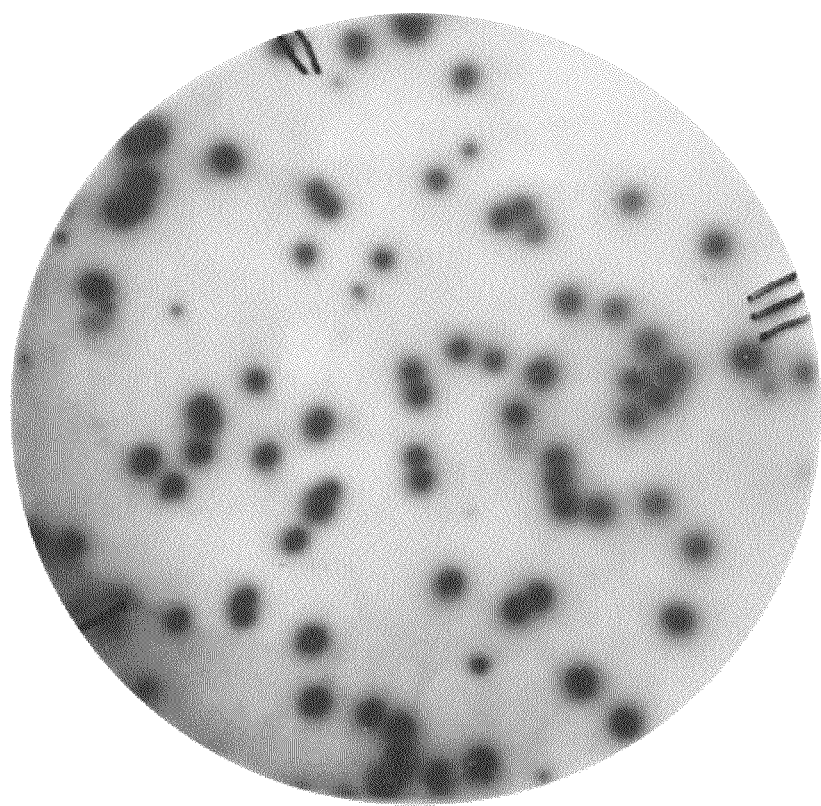

FIG. 2 shows an IgE screening of an expression cDNA library from bovine mammary glands. E. coli cells Y1090 infected with phages carrying the cDNA library were induced to synthesize recombinant proteins. These proteins were transferred to a nitrocellulose filter and exposed to serum IgE from milk allergic patients followed by incubation with 125I-labeled anti-human IgE antibodies. In this autoradiogram of the filter the IgE-reactive clones appear as black dots.

Figure 3:
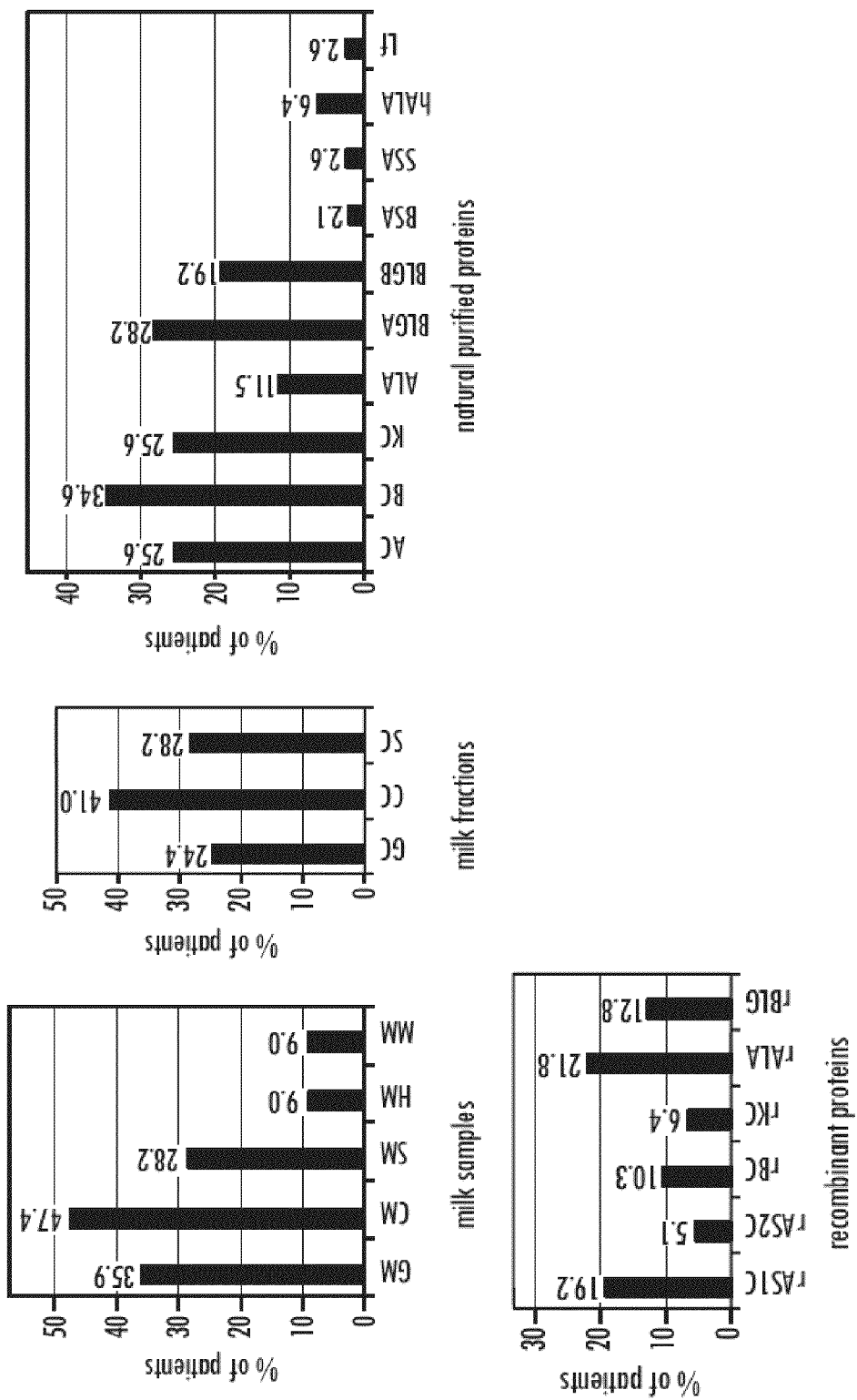

FIG. 3 shows the allergenic activity of the milk samples and components. Biological activity was determined in human RBL assays. The percentages of patients' sera (n=78) giving a positive reaction in human RBL assays are shown as black bars (y-axis). Analyzed were the following milk components: milk samples from different species (GM, goat's milk; CM, cow's milk; SM, sheep's milk; HM, human milk; MM, mare's milk), the casein fraction of different species (GC, goat casein; CC, cow casein; SC, sheep casein), natural purified proteins (ACalpha-casein; BC, beta-casein; KC, kappa-casein; ALA, alpha-lactalbumin, BLGB, beta-lactoglobulin variant B; BLGA, beta-lactoglobulin variant A; BSA, bovine serum albumin; SSA, sheep serum albumin; hALA, human alpha-lactalbumin; Lf, lactoferrin), recombinant proteins (rAS1C, recombinant alphaS1-casein; rAS2C, recombinant aS2-casein; rBC, recombinant beta-casein; rKC, recombinant kappa-casein; rALA, recombinant alpha-lactalbumin; rBLG, recombinant beta-lactoglobulin), recombinant fragments of BSA (F1, recombinant fragment 1 of BSA; F2, recombinant fragment 2 of BSA; F3, recombinant fragment 3 of BSA) and synthetic peptides of aS1-casein (Cast1-Cas6).

FIG. 4 shows a list of allergen sequences found in milk.

Figure 5:
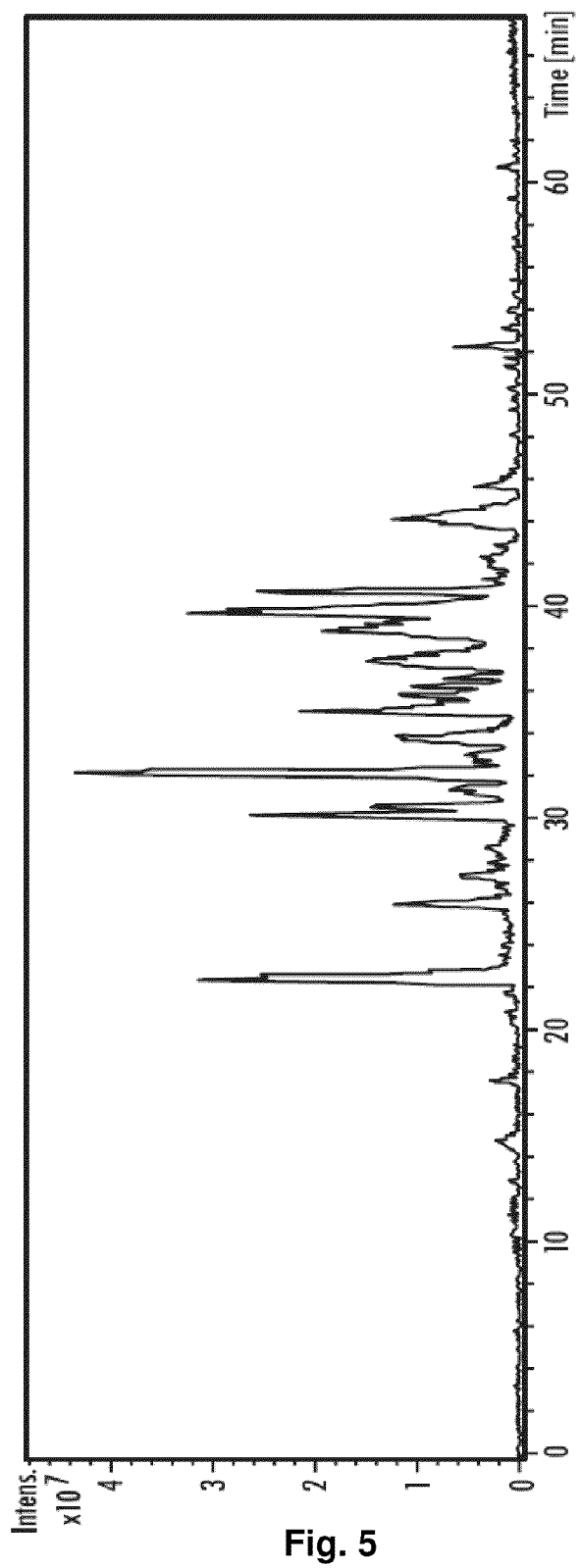

FIG. 5 shows the separation of a hydrolyzed milk formula using nano liquid chromatography followed by electrospray ionization MS. Presentation of total ion chromatogram of 1 µg hydrolyzed milk sample. Retention times are shown on the x-axis and signal intensities in cps (counts per second) are displayed on the y-axis.

FIG. 6 shows a Mascot search and the identification of beta-casein-derived peptides in hydrolyzed cow's milk.

Figure 7:
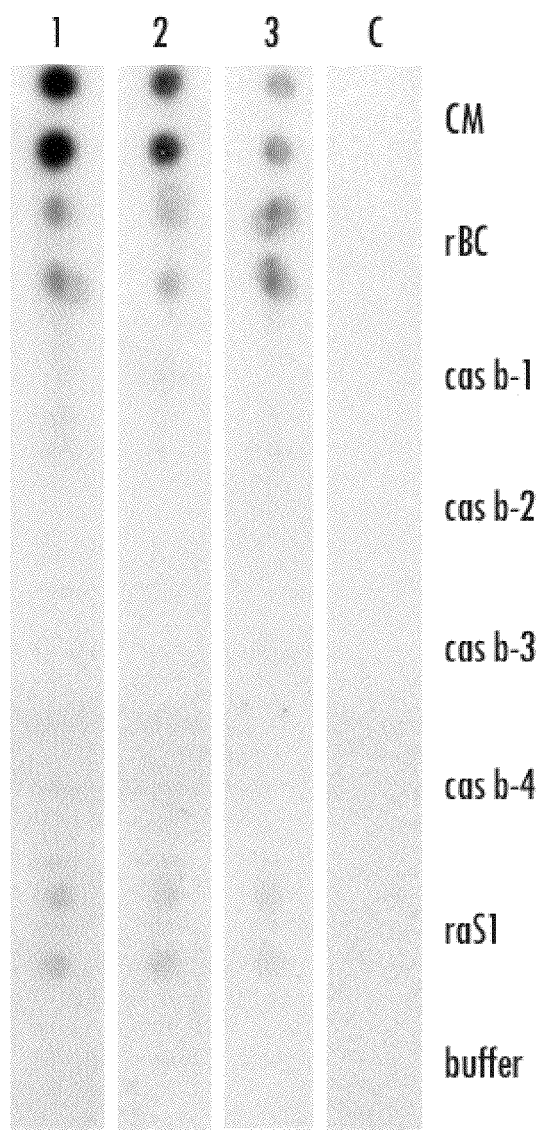

FIG. 7 shows beta-casein-derived peptides identified in hydrolyzed cow's milk as being not IgE-reactive.

DETAILED DESCRIPTION

One aspect of the present disclosure is to provide a method for identifying allergenic milk proteins and/or peptides comprising the steps of providing at least one expression library comprising DNA or cDNA derived from the mammary gland tissue of a lactating cow, expressing at least one protein or peptide encoded by said expression library, determining the binding capacity of said at least one protein or peptide to IgE of at least one serum of an individual who is sensitive to cow's milk, contacting the at least one protein or peptide exhibiting an IgE binding capacity with basophil cells, eosinophil cells or mast cells, and identifying the at least one protein or peptide as being allergenic when said basophil cells, eosinophil cells or mast cells release at least one mediator upon contact with the at least one protein or peptide.

The present disclosure also provides a method which comprises the following steps providing at least one expression library comprising DNA or cDNA derived from at least one allergen source, expressing at least one protein or peptide encoded by said expression library, determining the binding capacity of said at least one protein or peptide to IgE of at least one serum of an individual who is sensitive to the at least one allergen source, contacting the at least one protein or peptide exhibiting an IgE binding capacity with basophil cells, eosinophil cells or mast cells, and identifying the at least one protein or peptide as being allergenic when said basophil cells, eosinophil cells or mast cells release at least one mediator upon contact with the at least one protein or peptide.

The method according to the present disclosure is particularly suited to identify proteins and peptides exhibiting allergenic properties. In order to identify allergenic properties of proteins or peptides only amounts in the range of micrograms or nanograms are required. These proteins and peptides are encoded by a DNA or cDNA library which is obtained from a source which is known to synthesize proteins and/or peptides provoking an allergenic reaction in an individual. The allergen source may comprise different types of tissues and cells which may be responsible for the biosynthesis of the allergens. If these cells and tissues are known it is possible to specifically create DNA or cDNA libraries from said cells and tissues, which can be used in the method according to the present disclosure. For example, milk allergens from a mammal, in particular from a cow, can be identified by isolating DNA or cDNA from the mammary gland tissue of lactating mammals.

The expressed proteins and peptides of the DNA and cDNA expression library are contacted with IgE of at least one serum of at least one individual who is sensitive to the at least one allergen source. In this first step those proteins and peptides are identified which are capable to bind to IgE, which is one prerequisite for allergic reactions. The term "IgE-reactive" in accordance with the present disclosure means the capacity of an amino acid sequence to bind IgE. In a further step the peptides and proteins binding to IgE are further contacted with basophil cells, eosinophil cells or mast cells, which have been previously loaded with IgE from at least one individual which is known to be allergic against at least one allergen of the allergen source. Basophil cells, eosinophil cells or mast cells carrying allergen specific IgE molecules release upon contact with a respective allergen mediators such as histamine and/or other allergic mediators released by basophil cells, eosinophil cells or mast cells, which indicates that the peptides and proteins capable to bind to IgE are also capable to induce degranualtion of basophil cells, eosinophil cells or mast cells after being contacted with these cells. Suitable allergenic mediators preferably are histamine, heparin, prostaglandine, leukotriene, chemokines, cytokines. Other allergenic mediators that may be useful in the context of the present disclosure include β-hexosaminidase, eosinophil peroxidase, ribonuclease (RNase), deoxyribonuclease, lipase, plasminogen and major basic protein. The person skilled in the art is well aware of mediators released by these cells which can be identified by common textbook knowledge (see for example Janeway et al. 2002: Immunology, Spektrum Akademischer Verlag; Auflage: 5. Auflage; Paul et al. 1989: Fundamental Immunology, Raven Press Ltd.; Second edition).

Those members of the DNA or cDNA library which bind to IgE of an allergic individual and are capable to induce degranulation of basophil cells can be isolated and their DNA or cDNA insert can be sequenced by methods known in the art. Alternatively, the proteins and peptides expressed by the respective library members can be isolated by methods known in the art and analysed by mass spectrometry or amino acid sequencing, for instance.

The members of the DNA or cDNA library may be derived from any source carrying biological material which is known or unknown to provoke allergenic reactions when contacted with an individual. Hence, the term "allergen source" as used herein refers to any kind of biological material capable to synthesize allergens.

The term "peptide" or "protein" is intended to mean a sequence of amino acids held together by peptide bonds. "Peptide" as used herein means that the amino acid containing molecule contains essentially up to 250 amino acids, such as up to 200 amino acids, such as up to 150 amino acids, such as up to 100 amino acids, such as up to 50 amino acids, such as up to 45 amino acids, especially such as up to 40 amino acids, such as up to 30 amino acids, such as up to 20 amino acids, and preferably more than 2 amino acid residues. "Protein", as used herein, means that the amino acid containing molecule contains essentially more than 250 amino acids. In the upper range, the present disclosure may use the term protein and peptide for the same type of molecule.

Allergens (substances which are capable to provoke an allergenic reaction in an individual) are synthesized by various organisms, including plants and animals. According to a preferred embodiment of the present disclosure the at least one allergen source is an animal, more particularly a mammal Animals are known to be a source of allergens. These allergens are usually present in animals (e.g. cat and dog) dander or skin flakes, as well as their saliva and urine. Mammals, for instance, secrete allergens also in milk. Consequently mammals like cow, horse and buffalo may comprise a high amount of allergens. The cDNA and DNA used to identify such allergens may be isolated from lactating mammals, whereby the DNA or cDNA is preferably obtained from the mammary gland tissue.

Another source of allergens are mites like house dust mites, fish, egg etc. These animals are known to produce substances which cause allergic reaction in individuals.

A further allergen source are plants. In particular weeds and nuts are known to produce allergens. Of course also trees, like birch, are a source of allergens.

The DNA (such as genomic DNA and other types of DNA with the exception of cDNA) or cDNA can be obtained from the allergen source such as cow milk or nutritional formulations containing cow milk by methods known in the art. These nucleic acid molecules are preferably obtained from cells and tissues which are known or suspected to produce allergens. However, in order to reduce the amount of clones to be screened to identify allergens it is preferred to insert cDNA molecules (cDNA molecules are derived from mRNA) into expression libraries, because these molecules reflect the pool of proteins and peptides expressed in the respective cells and tissue. In accordance with the present disclosure, any method may be used to prepare a cDNA from a cell that expresses (potentially) the allergen. Such methods are well-known to a person of skill in the art (see, for example, Sambrook et al., "Molecular Cloning: A Laboratory Manual," 2nd ED. (1989) and Ausubel, F. M. et al., "Current Protocols in Molecular Biology," (Current Protocol, 1994)). There are also numerous commercially available kits for obtaining double-stranded cDNA, for example, the Superscript II or Superscript III kit (Invitrogen, USA, catalog #18580008), the Great Lengths cDNA Synthesis Kit (Clontech, USA, catalog #K-1048-1), the cDNA Synthesis Kit (Stratagene, USA, catalog #200301), and the like.

The cDNA and DNA molecules may be ligated to linker DNA sequences containing suitable restriction enzyme recognition sites. Such linker DNAs are also known in the art and commercially available, for example, from Promega Corporation, USA and from New England Biolabs, USA. The cDNA and DNA molecules may be further subjected to restriction enzyme digestion, size fractionation on columns or gels, or any other suitable method known to a person of ordinary skill in the art.

The cDNA and DNA library is then inserted into expression vectors which may comprise a nucleotide sequence encoding a tag, sequences that direct DNA replication in bacterial cells, sequences that direct DNA transcription and mRNA translation in eukaryotic cells and the like. Suitable expression vectors which comprise the described regulatory elements are known in the art. The cDNA or DNA molecule as described herein above may be designed for direct introduction or for introduction via liposomes, phage vectors or viral vectors (e.g. adenoviral, retroviral) into a cell. A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside. ("IPTG"). For recombinant expression and secretion, the cDNA or DNA molecule of interest may be ligated (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Alternatively, the recombinant protein or peptide can be expressed in stable cell lines that contain the gene construct integrated into a chromosome. The co-transfection with a selectable marker such as dhfr, gpt, neomycin, hygromycin allows the identification and isolation of the transfected cells. The expression vectors will preferably include at least one selectable marker. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, 293 and Bowes melanoma cells; and plant cells. Appropriate culture mediums and conditions for the above-described host cells are known in the art. The insertion of the cDNA and DNA library (cDNA or DNA pool of a specific cell or tissue) molecules into expression vectors results in expression libraries.

The expression library used to express the cDNA and DNA molecules of the allergen source is preferably a phage display library or a bacterial expression library. The members ("constructs") of these libraries are then inserted into cells capable to express the proteins and peptides encoded by the cDNA and DNA. Preferred cells are selected on the type of vectors used to create the cDNA and DNA libraries. If the vectors are designed for bacterial expression, the cells are bacterial cells. The cDNA and DNA libraries are introduced into the cells using methods (e.g. transformation), well-known to a person of ordinary skill in the art and described, e.g., in Sambrook et al., Molecular Cloning: a Laboratory Manual, 2nd Ed., Cold Spring Harbor Press (Cold Spring Harbor, N.Y., 1989). The next steps of culturing bacterial cells to select for transformants and to produce individual bacterial colonies (clones) are well known in the art. Following selection of transformants on agar plates, the cultured bacterial colonies may be picked individually and used to innoculate liquid culture media arranged in arrays in a grid pattern to form gridded bacterial stocks, for example, in 96-well microtiter plates. This arrangement allows representative growth of each bacterial clone in an independent well and facilitates subsequent sub-selection of positive scoring pools of clones.

It is particularly preferred to use vectors for the expression library which are able to secrete the produced proteins and peptides to the exterior of the cell. The secreted proteins and peptides may further comprise a membrane anchoring domain which allows to immobilise the expressed molecules on the surface of the cells. Methods and means to produce such libraries are known to the person skilled in the art.

In order to determine the binding of allergen specific IgE molecules to the peptides and/or proteins encoded by the cDNA and DNA libraries the at least one protein or peptide is immobilized on a solid support. The solid support is afterwards contacted with IgE molecules derived from individuals suffering from an allergy and the binding of said IgE molecules on said solid support is determined.

The binding of IgE to proteins and peptides immobilized on a solid support can be achieved by using antibodies or fragments thereof capable to bind to IgE. Such antibodies are well known in the art.

The solid support to be used according to the present disclosure may be a membrane, preferably a nitrocellulose membrane. In a particularly preferred embodiment these membranes are contacted with the bacterial colonies carrying the cDNA or DNA library present on an agar plate in order to form a replica of these colonies. This replica may be used to detect binding of allergen specific IgE to specific colonies.

Basophil cells, eosinophil cells or mast cells which have been loaded with allergen specific IgE from individuals suffering from an allergy can be used to determine the allergenic potential of the proteins or peptides encoded by the DNA or cDNA library. The basophil cells, eosinophil cells or mast cells may be of any mammal origin, whereby it is preferred to use humanized rat basophil leukaemia (RBL) cells (e.g. clone RBL-703/21). Cells can be humanized by introducing and expressing DNA that encodes all or a portion of a human Fc-receptor, preferably DNA that encodes all or a portion of a human IgE-receptor I. Methods for the production of humanized cells are known in the art. Preferably the method as described in Hoffmann et al. (loc. lit.) is used for the production of humanized cell cultures. Methods for the production of stripped basophils are described in or Kleine Budde et al. (Int Arch Allergy Immunol, 126(4)).

After the identification of the proteins/peptides which are able to bind to allergen specific IgE the amino acid sequence of the at least one protein or peptide exhibiting an IgE binding capacity as determined in step c) is preferably determined and the at least one protein or peptide which is able to bind to allergen specific IgE is chemically synthesized or recombinantly produced prior to step d) and may be used in step d).

According to a preferred embodiment of the present disclosure, the method further comprises a step of determining the amino acid sequence of the at least one protein or peptide identified in step e).

The amino acid sequence of the proteins or peptides encoded and expressed by the DNA or cDNA library may be determined by mass spectrometry or by Edman degradation. If such a method is used, the proteins and/or peptides expressed by the DNA or cDNA library have to be isolated prior to amino acid sequencing. The isolation may be achieved by methods known in the art. In order to facilitate the isolation of the proteins and peptides they may be fused to a tag (e.g. histidine tag). Alternatively, it is also possible to isolate the respective DNA or cDNA clone and to sequence the DNA or cDNA insert.

Suitable methods for determining an amino acid sequence of the proteins and peptides include, but are not limited to, Edman degradation, (tandem) mass spectrometry and the like (see e.g. Edman, P. Mol. Biol. Biochem. Biophys., (1970), 8: 211-255; U.S. Pat. No. 6,799,121). The amino acid sequence of the proteins and peptides may be compared to amino acid sequences of known proteins.

The term "mass spectrometry" as used herein includes various methods such as tandem mass spectrometry, matrix assisted laser desorption ionization (MALDI) time-of-flight (TOF) mass spectrometry, MALDI-TOF-TOF mass spectrometry, MALDI Quadrupole-time-of-flight (Q-TOF) mass spectrometry, electrospray ionization (ESI)-TOF mass spectrometry, ESI-Q-TOF, ESI-TOF-TOF, ESI-ion trap mass spectrometry, ESI Triple quadrupole mass spectrometry, ESI Fourier Transform mass spectrometry (FTMS), MALDI-FTMS, MALDI-Ion Trap-TOF, and ESI-Ion Trap TOF. These mass spectrometry methods are well known in the art (see e.g. Gary Siuzdak, "Mass Spectrometry for Biotechnology", Academic Press, NY, (1996)). At its most basic level, mass spectrometry involves ionizing a molecule and then measuring the mass of the resulting ion. Since molecules ionize in a way that is well known, the molecular weight of the molecule can generally be accurately determined from the mass of the ion. Tandem mass spectrometry, for instance, may be used to identify proteins because it can provide information in addition to parent ion molecular weight. Tandem mass spectrometry involves first obtaining a mass spectrum of the ion of interest, then fragmenting that ion and obtaining a mass spectrum of the fragments. Tandem mass spectrometry thus provides both molecular weight information and a fragmentation pattern that can be used in combination along with the molecular weight information to identify the exact sequence of a peptide or protein (see e.g. Hunt et al. (1986) PNAS USA 83:6233-6237; Shevchenko et al. (1996) PNAS USA 93:14440-14445; Figeys et al. (1996) Anal. Chem. 68:1822-1828 and Wilm et al. (1996) Nature 379:466-469.

As mentioned, another embodiment of the present disclosure relates to a method for identifying allergenic milk proteins and/or peptides comprising the steps of providing at least one expression library comprising DNA or cDNA derived from the mammary gland tissue of a lactating cow, expressing at least one protein or peptide encoded by said expression library, determining the binding capacity of said at least one protein or peptide to IgE of at least one serum of an individual who is sensitive to cow's milk, contacting the at least one protein or peptide exhibiting an IgE binding capacity with basophil cells, eosinophil cells or mast cells, and identifying the at least one protein or peptide as being allergenic when said basophil cells, eosinophil cells or mast cells release at least one mediator upon contact with the at least one protein or peptide.

In another embodiment of the disclosure the method further comprises a step of determining the amino acid sequence of the at least one protein or peptide identified by the method previously discussed. Thus, the method of the disclosure for identifying allergic proteins and/or peptides described above is preferably employed for the identification of allergic milk proteins and/or peptides. Accordingly, all of the above definitions and preferred embodiments also apply to this embodiment of the disclosure.

Figure 1A:
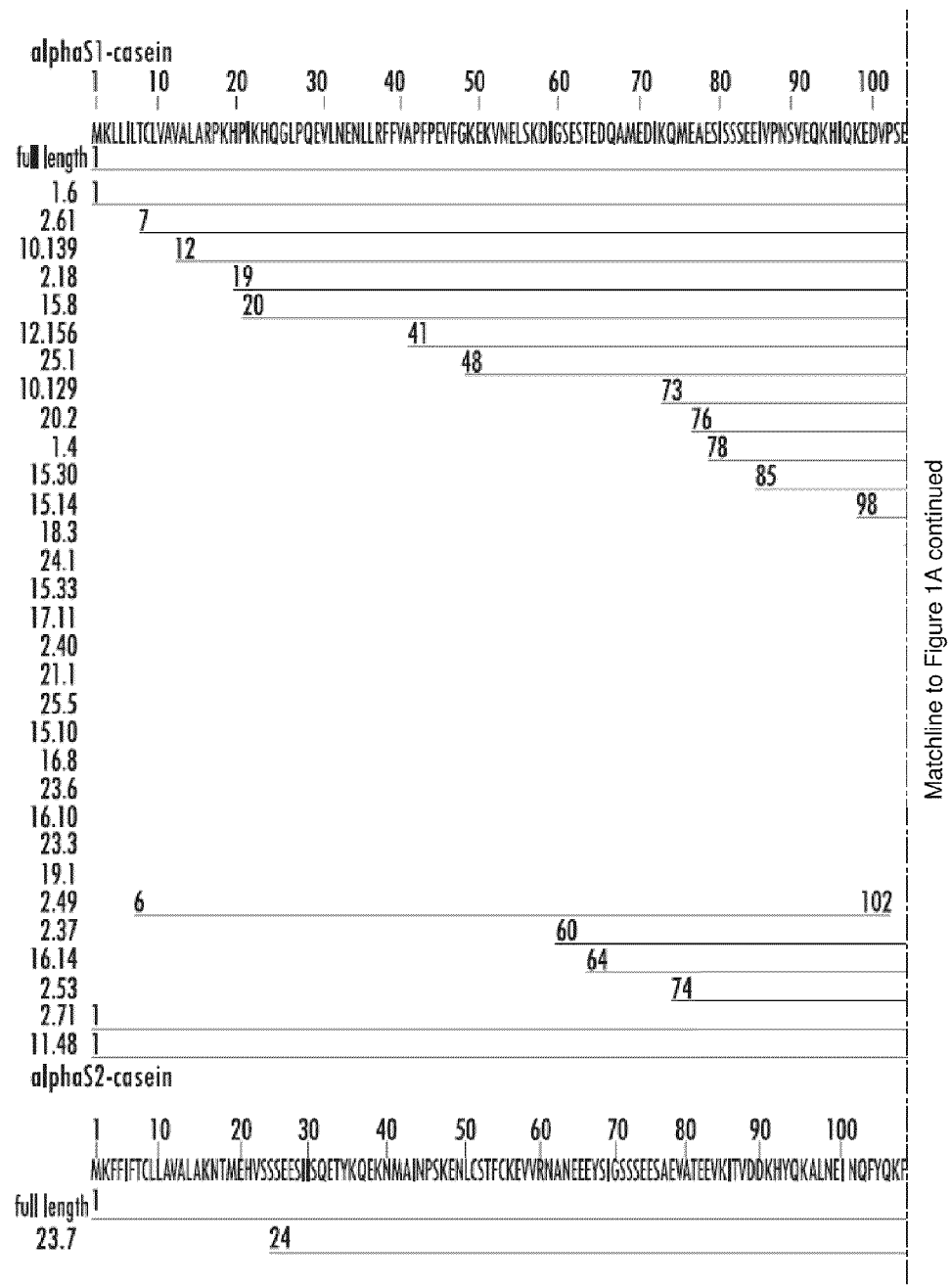
FIG. 1A shows the deduced amino acid sequences of cDNAs encoding IgE-reactive full-length alphaS1- and alphaS2-casein and IgE-reactive alphaS1- and alphaS2-casein fragments. The amino acid sequence of full-length alphaS1- and alpha-S2-casein are shown at the top. The sequence of IgE-reactive alphaS1- and alphaS2-casein fragments (clone numbers right margin) are displayed as lines. Numbers indicate the first and last amino acid of each clone.
Figure 1B:
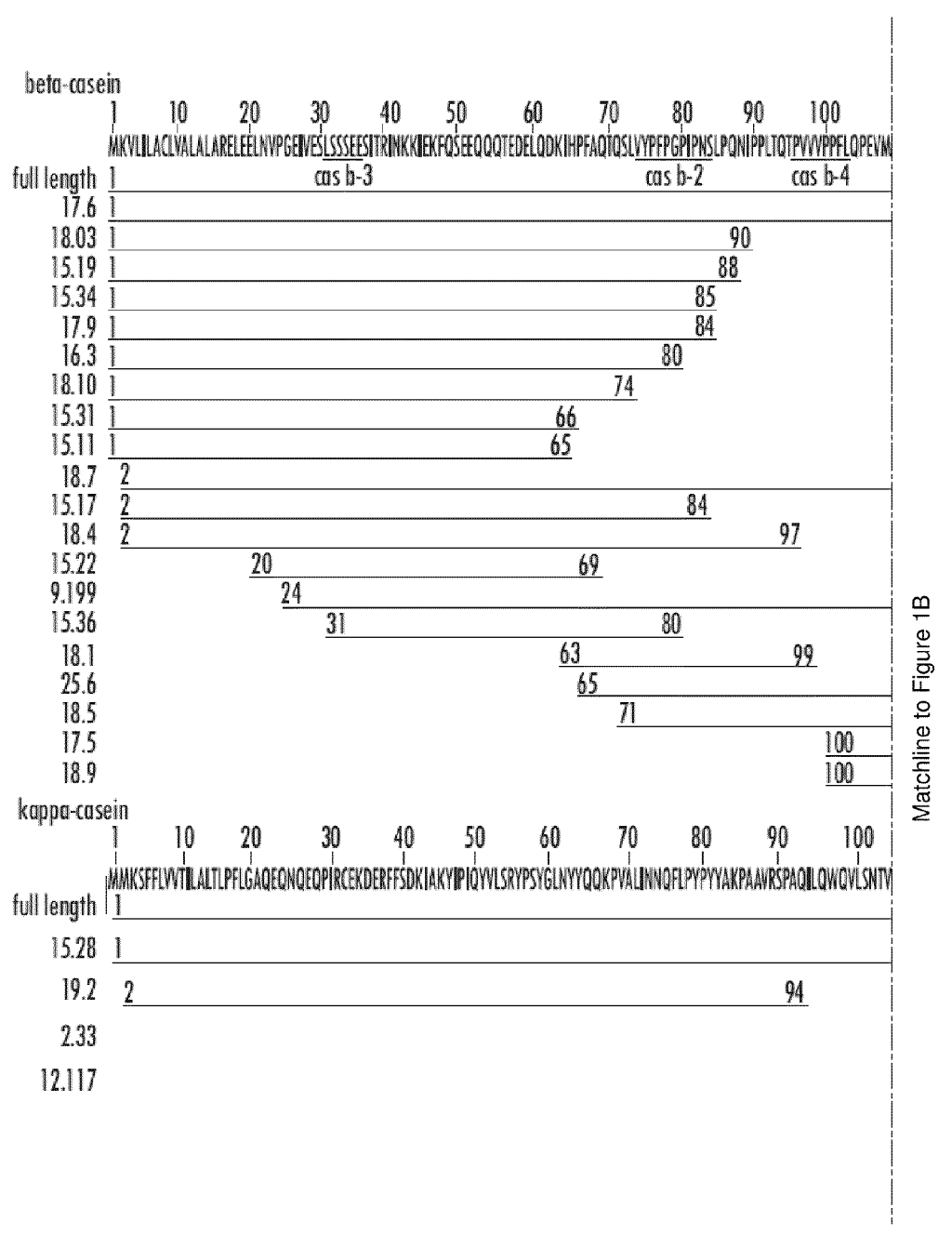

A further embodiment of the present disclosure relates to a method for determining the allergenicity of a cow milk comprising sample comprising the step of determining the presence of at least one of the proteins and peptides of FIGS. 1A, 1B and 1C (SEQ ID Nos. 22-84) and Table 1A, 1B and Table 2 (SEQ ID Nos. 1-21). The term "cow milk comprising sample" in accordance with the present application refers to a food sample or a nutrition sample containing cow milk. Non-limiting examples are cow milk, curd, cream, butter, yoghourt and food containing any of these. Within said cow milk comprising sample said at least one of the proteins and peptides is present in an amount which allows for determining the allergenicity of a cow milk comprising sample. Usually amount in the range of micrograms or nanograms of a protein or peptide is sufficient to determine allergenicity.

The proteins and peptides identified in FIGS. 1A, 1B and 1C (SEQ ID Nos. 22-84) and Table 1A, 1B and Table 2 (SEQ ID Nos. 1-21) can be used to determine whether a sample comprising cow milk comprises allergenic molecules. If only one of said proteins or peptides is present in a cow milk comprising sample, the sample is considered as being allergenic.

The method of the present disclosure is particularly suited to determine the allergenity of a hydrolysed cow milk.

The at least one protein and peptide is preferably determined by an immunoassay involving antibodies or fragments thereof binding to the proteins and peptides identified in FIGS. 1A, 1B and 1C (SEQ ID Nos. 22-84) and Table 1A, 1B and Table 2 (SEQ ID Nos. 1-21).

The at least one protein and/or peptide is preferably determined by mass spectrometry. In order to identify the cow milk components present in a sample comprising cow milk mass spectrometry may be applied. Mass spectrometry allows to identify the milk components as identified in FIGS. 1A, 1B and 1C (SEQ ID Nos. 22-84) and Table 1A, 1B and Table 2 (SEQ ID Nos. 1-21). A comparison between the fragments present in the sample with the proteins and peptides of FIGS. 1A, 1B and 1C (SEQ ID Nos. 22-84) and Table 1A, 1B and Table 2 (SEQ ID Nos. 1-21) allows to determine whether said sample comprises allergenic substances derived from cows milk.

In order to achieve better results the proteins and peptides present in the sample are preferably isolated prior to mass spectrometry. This isolation may be done by an electrophoretic method, preferably two-dimensional electrophoresis, or high performance liquid chromatography.

Screening of product/proteins/peptides in the IgE binding assay (step c)) and basophil (humanized mast cells) degranulation indeed provides data on potential allergenicity, and these methods are used in clinical practice. However, the cDNA expression library data will add a complete list of potential allergenic peptides/peptide sequences for particular allergens (e.g. cow's milk). The present disclosure combines these methods (improved detection of potential allergenic structures), enabling using mass spectrometry to verify the presence of these potential allergenic structures in product matrices. This combination of a sequence database of allergenic milk proteins and peptides established in combination with IgE reactivity and degranulation (bioactivity) should serve as a basis for the development of a more reliable, sensitive and reproducible method for the assessment and prediction of allergenicity of products containing milk. Although, a similar method has been used to for the identification of grass pollen allergens (Ball et al. 1994, Journal of Biological Chemistry, Vol. 269; Issue of November 11, p. 28323-28328) the findings of the present disclosure are nevertheless surprising, as the skilled person would not have considered that the method according to the teachings of Ball et al. 1994 or a similar method could successfully be applied to milk allergens. To explain further, IgE-binding of grass pollen allergens as well as Ig-E binding to other respiratory allergens depends critically on amino acid residues which are spread over the allergen. Thus, grass pollen allergens and respiratory allergens in general assemble into conformational (discontinous) IgE epitopes. Vrtatla et al. (J. Clin. Invest, Vol 99, No 7, p. 1673-1681) show that loss of this conformation, e.g. in recombinant fragments derived from conformational allergens, leads to drastically reduced capacity of IgE-binding and histamine release from patients' basophils. In contrast to grass pollen allergens and respiratory allergens, milk allergens and food allergens in general have epitopes which are not conformational but unfolded (Järvinen et al., Int Arch Allergy Immunol, Vol 126, p. 111-118 and Järvinen et al., Allergy, Vol 62, p. 758-765). The prior art thus only recognized IgE-binding of unfolded allergens derived e.g. from milk and egg. The release of a mediator from basophil cells, mast cells, or eosinophil cells has not been shown or suggested to the knowledge of the inventors. Considering the teaching of Vrtatla et al (loc. lit.) the skilled person would assume that fragments of allergens and recombinantly produced allergens of milk which do not have IgE-reactivity would also not have the capacity to induce histamine release from patients' basophils. Similarly, considering the teaching of Vrtatla et al (loc. lit.) the skilled person would assume that fragments of allergens and recombinantly produced allergens of milk which do have IgE-reactivity would also have the capacity to induce histamine release from patients' basophils. The step of further testing histamine release of IgE reactive milk proteins and peptides therefore appeared, according to the prior art, dispensible. In contrast, the inventors have surprisingly found that only a method including the steps of IgE reactivity and release of a mediator from basophil cells, mast cells or eosinophil cells can reliably identify allergenic milk proteins and peptides. It is further noted that only the combined testing of IgE reactivity and release of a mediator allows for the reliable assessment of allergenicity of a protein or peptide derived form milk. Depending on the individual to be tested proteins and peptides can either induce the release of a mediator or not. Thus, non-allergenic proteins and peptides which only display IgE-reactivity without mediating release of a mediator from basophil cells, mast cells or eosinophil cells can be distinguished from allergenic proteins or peptides (allergens). Therefore, only the method according to the disclosure can reliably assess allergenicity of a protein or peptide of the disclosure for a particular individual, i.e. specifically distinguish between non-allergenic IgE. It was in particular surprising that the methods of the disclosure led to the identification of the peptides indicated in Tables 1A, 1B and Table 2 (SEQ ID Nos. 1-22), since these peptides are all unfolded peptides and hence do not have conformational epitopes.

An improved method to detect potential allergens by using the cDNA expression library followed up a phage peptide expression system and functional screening using IgE binding and IgE mediated basophil cell degranulation, eosinophil cell degranulation or mast cell degranulation. This approach enables monitoring/screening and forecasting the presence of potential food allergens in raw materials, ingredients and finished product for the purpose of developing and manufacturing nutritional formulations.

The allergenic proteins or peptides specifically disclosed herein or identified by the described methods of the disclosure may be used to diagnose an allergy or an predisposition to an allergy in a individual, preferably a milk allergy or predisposition for a milk allergy. Accordingly, in one embodiment the disclosure relates to a method for the diagnosis of an allergy or a predisposition to an allergy in an individual comprising administering at least one allergenic protein or peptide specifically disclosed herein or identified by the methods described herein to an individual suspected of being allergic or becoming allergic and assessing whether the individual developed an allergic reaction against the protein or peptide. Means and ways of administration are described herein below.

The diagnosis of an allergy involves in general having a skin or blood test to find out what substance, or allergen, may trigger an allergic response in an individual. Skin tests are usually preferred because they are rapid, reliable, and generally less expensive than blood tests, but either type of test may be used. For a skin test a suitable amount of at least one allergenic protein or peptide specifically disclosed herein or identified by the methods described herein is placed on or below the skin to determine if a allergic reaction develops. There are three types of skin tests preferred: (1) The skin prick test is done by placing a drop of a solution containing said at least one allergenic protein or peptide (allergen solution) on the skin, and a series of scratches or needle pricks allows the solution to enter the skin. If the skin develops a red, raised itchy area (called a wheal), it usually means that the person is allergic to that allergen. This is called a positive reaction. (2). During the intradermal test, a small amount of the allergen solution is injected into the skin. An intradermal allergy test may be done when a substance does not cause a reaction in the skin prick test but is still suspected as an allergen for that person. (3) For a skin patch test, the allergen solution is placed on a pad that is taped to the skin for about 24 to 72 hours. This test is used to detect a skin allergy called contact dermatitis. In a blood test an allergy in an individual may be determined by the steps of (i) contacting at least one protein or peptide identified by the methods of the disclosure or specifically disclosed herein with a blood sample, serum sample or plasma sample from said individual, and (ii) determining if said at least one protein or peptide binds to an IgE antibody in said blood sample, serum sample or plasma sample, wherein binding of said at least one protein or peptide to an IgE antibody is indicative of an allergy or a predisposition of an allergy in said individual; and/or (i') contacting at least one protein or peptide identified by the methods of the disclosure or specifically disclosed herein with basophil cells, eosinophil cells or mast cells of said individual, and (ii') determining if said basophil cells, eosinophil cells or mast cells release upon contact with the at least one protein or peptide at least one mediator, or degranulate upon contact with the at least one protein or peptide, wherein release of said at least one mediator upon contact with said at least one protein or peptide or degranulation upon contact with said at least one protein or peptide is indicative of an allergy or a predisposition for an allergy in said individual.

In addition and according to another embodiment of the disclosure, the allergenic proteins or peptides specifically disclosed herein or identified by the described methods of the disclosure may be used in an allergen-immunotherapy of an allergy in an individual. Accordingly, an embodiment of the disclosure relates to a method for allergen-immunotherapy of an allergy in an individual comprising administering at least one allergenic protein or peptide specifically disclosed herein or identified by the methods described herein. It is preferred that the allergy is a milk allergy.

Allergen-immunotherapy (also termed hyposensitization therapy, immunologic desensitization or allergen-specific immunotherapy) in accordance with the present disclosure is a form of immunotherapy for allergic disorders in which the patient is vaccinated with increasingly larger doses of an allergen with the aim of inducing immunologic tolerance. Allergen-immunotherapy is the only treatment strategy which treats the underlying cause of the allergic disorder. It is a highly cost effective treatment strategy which results in an improved quality of life and a reduction in allergic and allergen related symptoms. Immunotherapy has been shown to produce long term remission of allergic symptoms, reduce severity of associated allergic reactions as well as reduce the chances of developing new sensitizations to allergens. This is achieved via immunotherapy modulating the immune system response to allergens. Allergen immunotherapy can either reduce the need for medication, severity of symptoms or eliminate hypersensitivity altogether. Moreover, allergen-specific immunotherapy is the only treatment option that is known to modify the allergy disease process (with a possible chance of curing the disease), whereas other therapies merely suppress the symptoms.

It is preferred that the at least one protein or peptide of the disclosure for use in any of the herein described methods or uses for diagnosing or methods and uses of allergen immunotherapy is present in a pharmaceutical composition. In accordance with the present disclosure, the term "pharmaceutical composition" relates to a composition for administration to a patient, preferably a human patient. The pharmaceutical composition of the disclosure comprises the compounds recited above. It may, optionally, comprise further molecules capable of altering the characteristics of the compounds of the disclosure thereby, for example, stabilizing, modulating and/or activating their function. The composition may be in solid, liquid or gaseous form and may be, inter alia, in the form of (a) powder(s), (a) tablet(s), (a) solution(s) or (an) aerosol(s). The pharmaceutical composition of the present disclosure may, optionally and additionally, comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, organic solvents including DMSO etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician. The pharmaceutical composition for use in accordance with the present disclosure can be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. The pharmaceutical composition may, accordingly, be administered orally, parenterally, such as subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable excipients. The pharmaceutical composition of the disclosure can be administered as sole active agent or can be administered in combination with other agents.

In another embodiment the disclosure relates to a method for determining an allergy or a predisposition for an allergy in an individual comprising contacting at least one protein or peptide disclosed herein or identified by the methods described herein with basophil cells, eosinophil cells or mast cells isolated from said individual, and identifying the at least one protein or peptide as being allergenic in said individual when said basophil cells, eosinophil cells or mast cells release upon contact with the at least one protein or peptide at least one mediator, or degranulate upon contact with the at least one protein or peptide. In a preferred embodiment of the disclosure the allergy or predisposition is a milk allergy or a predisposition to a milk allergy. In a further preferred embodiment of the disclosure these methods for diagnosing an allergy or a predisposition to an allergy further comprises discriminating individuals with a severe allergy from individuals which are sensitized but asymptomatic, and/or discriminating individuals who grow out of an allergy from individuals who do not grow out an allergy. In this regards, the term "to grow out of an allergy" means that the allergy is not persistent but will decrease or preferably disappear when then individual having the allergy is becoming older. In this regard is preferred that the subject grows out of allergy during childhood and is not allergic as adult subject.

The at least one protein or peptide of the method for determining an allergy or a predisposition for an allergy in an individual may be immobilized on a solid support (e.g. nitrocellulose). The solid support is afterwards contacted with basophil cells, eosinophil cells or mast cells isolated from said individual and the release of a mediator or degranulation is determined. Alternatively, the cells may be immobilized on a solid support and contacted with the at least one protein or peptide. Moreover, the at least one protein or peptide may be a protein or a peptide isolated from its natural source or a recombinant protein or peptide produced by the methods described herein above In another embodiment the disclosure relates to a method for identifying a IgE-reactive non-allergenic milk protein or peptide encoded by a DNA or cDNA of at least one expression library comprising the steps of: providing at least one expression library comprising DNA or cDNA derived from the mammary gland tissue of a lactating cow, expressing at least one protein or peptide encoded by said expression library, determining the binding capacity of said at least one protein or peptide to IgE of at least one serum of an individual who is sensitive to cow's milk, contacting the at least one protein or peptide exhibiting an IgE binding capacity as determined in step c) with basophil cells, eosinophil cells or mast cells and determining if said basophil cells, eosinophil cells or mast cells (i) release upon contact with the at least one protein or peptide at least one mediator, or (ii) degranulate upon contact with the at least one protein or peptide, wherein release of the at least one mediator upon contact with the at least one protein or peptide or degranulation upon contact with the at least one protein or peptide is indicative for an allergy or a predisposition for an allergy in said individual. In this regard, it is noted that a non-allergenic milk protein or peptide is in general IgE-reactive but does not trigger the release of a mediator from basophil cells, eosinophil cells or mast cells or does not trigger degranulation of basophil cells, eosinophil cells or mast cells upon contact with said cells. Consequently, whether a milk protein or peptide is allergenic or non-allergenic can be determined by the methods of the disclosure. Non-allergenic milk proteins or peptides are defined by their IgE-reactivity but a lack of allergenic activity on these cells.

The IgE-reactive non-allergenic milk proteins or peptides identified by the method according to the disclosure may be used to saturate mast cell-bound IgE prior to allergen exposure and may be useful candidates for a safe immunotherapy of allergic diseases. Accordingly, the disclosure relates in another embodiment to a method for the treatment of an allergy in an individual comprising administering at least one IgE-reactive non-allergenic milk protein or peptide to said individual. It is preferred that the at least one IgE-reactive non-allergenic protein or peptide is formulated in a pharmaceutical composition as described herein above.

The examples illustrate the invention. The broad scope of this invention is best understood with reference to the following examples, which are not intended to limit the inventions to the specific embodiments.

EXAMPLES

Example 1

Identification of cDNA Sequences Coding for IgE-Reactive Milk Components and Fragments Thereof For identification of IgE-reactive proteins and IgE-reactive protein fragments contained in cow's milk an expression cDNA library using mammary gland tissue from a lactating cow was first constructed. This library was screened with the sera of cow's milk allergic patients. cDNAs coding for IgE-reactive full length alphaS1-, alphaS2-, beta-, kappa-casein and beta-lactoglobulin as well as IgE-reactive fragments thereof were identified. This is a rather surprising result as the mammalian proteins were produced in a bacterial system that does not add eukaryotic post translational modifications that may sometimes play a role in IgE binding as reported for major house dust mite allergens (Jacquet et al., 2002). The deduced amino acid sequences are shown in FIG. 1A-C (SEQ ID Nos. 22-84). The obtained IgE-reactive allergen fragments allow drawing conclusions about the location of IgE epitopes.

Experimental Protocol

Bovine mammary glands were obtained from a cow (race "Fleckvieh") and fresh tissue was immediately frozen and stored at −80° C. until use. Total RNA from the tissue was isolated and cDNA obtained using a cDNA Synthesis System. The purified cDNA was inserted into lambda phages using the Lambda gt11/EcoR I/CIAP-Treated/Gigapack III Cloning Kit (Stratagene, La Jolla, Calif.). *E. coli* Y1090 cells were infected with the phage library, plated onto LB Amp plates (145 mm diameter). Bacterial protein expression was induced by applying a nitrocellulose membrane (Whatman Schleicher & Schuell, Dassel, Germany). The adsorbed proteins were incubated with sera from CMA patients and bound IgE antibodies were detected with a $^{125}$I-labeled anti-IgE antibody (IBL, Hamburg, Germany). Membranes were exposed to X-ray films (Kodak, Rochester, N.Y.). Positive clones whose proteins were capable of binding human IgE appeared as dark spots on the X-ray films (an example of an autoradiogram of such a membrane is shown in FIG. 2).

Phage DNA of the positive clones was amplified using lambda gt11 forward primer (5' CGG GAT CCC GGT TTC CAT ATG GGG ATT GGT GGC GAC GAC TCC TGG AGC CCG TGA GTA TCG GCG GAA TTC 3') and lambda gt11 reverse primer (5' GAA TTC CAG CTG AGC GCC GGT CGC TAC CAT TAC CAG TTG GTC TGG TGT CAA CGG GAT CGC CG 3') and the amplified PCR products were sequenced. The obtained nucleotide sequences were analyzed by comparing them with a sequence database (http://www.ncbi.nlm.nih.gov/BLAST/).

Example 2

Discrepancy of Allergenic Activity and IgE Reactivity of Milk Components

In order to evaluate whether a molecule has allergen potential, not only its IgE reactivity but also its biological activity needs to be demonstrated. A scientifically approved model to test biological reactivity of molecules is induction of histamine release from human basophil granulocytes (Purohit 2005). For this purpose a rat basophil leukaemia cell line expressing the α-chain of the human FcεRI receptor (Hoffmann et al., Int Arch Allergy Immunol, Vol 126(4), p. 277-285) was used. Different milk components (n=33) including whole milk extracts from different species, milk fractions, purified natural and recombinant cow's milk proteins, and recombinant protein fragments were tested. The percentages of 78 patients whose serum IgE antibodies trigger β-hexosaminidase release of the humanized RBL cells in response to the individual milk components were determined (FIG. 3).

The most potent cell-activating component was cow's milk with a stimulation rate of 47.4% (FIG. 3, panel "milk samples"). But also goat's and sheep's milk gave values of 35.9 and 28.2%, respectively, confirming cross-reactivity of milk proteins from different species. Of the single components, the purified proteins, the caseins (AC, BC, KC) as well as beta-lactoglobulin A (BLGA) showed the highest activities and triggered a release in case of 25 to 34.6% of the patients' sera. Interestingly, the recombinant form of alpha-lactalbumin (rALA) triggered a much higher release than its natural counterpart. Each of the synthetic peptides had a rather low cell activating potential as stimulation rates of 2.6 to 7.7% were reached. The biological activity was compared to IgE reactivity (Table 2).

TABLE 2

IgE binding capacity and biological activity of milk components; discrepancy between IgE and allergic activity of milk components. Milk components show higher IgE reactivity than allergenic activity in human RBL assays.

| | | biological activity (% of patients) | IgE binding (% of patients) |
|---|---|---|---|
| milk samples | GM | 35.9 | 69.2 |
| | CM | 47.4 | 85.9 |
| | SM | 28.2 | 82.1 |
| | HM | 9.0 | 17.9 |
| | MM | 9.0 | 29.5 |
| casein fractions | GC | 24.4 | 46.2 |
| | CC | 41.0 | 52.6 |
| | SC | 28.2 | 46.2 |
| natural pruified proteins | AC | 25.6 | 50.0 |
| | BC | 34.6 | 44.9 |
| | KC | 25.6 | 30.8 |
| | ALA | 11.5 | 65.4 |

TABLE 2-continued

IgE binding capacity and biological activity of milk components;
discrepancy between IgE and allergic activity of milk components.
Milk components show higher IgE reactivity than allergenic
activity in human RBL assays.

|  |  | biological activity (% of patients) | IgE binding (% of patients) |
|---|---|---|---|
|  | BLGA | 28.2 | 50.0 |
|  | BLGB | 19.2 | 51.3 |
|  | BSA | 2.1 | 6.4 |
|  | SSA | 2.6 | 1.3 |
|  | hALA | 6.4 | 30.8 |
|  | Lf | 2.6 | 5.1 |
| recombinant proteins | rAS1C | 19.2 | 48.7 |
|  | rAS2C | 5.1 | 9.0 |
|  | rBC | 10.3 | 55.1 |
|  | rKC | 6.4 | 21.8 |
|  | rBLG | 12.8 | 23.1 |
|  | rALA | 21.8 | 25.6 |
| recombinant BSA fragments | BSA_F1 | 4.3 | 2.1 |
|  | BSA_F2 | 4.3 | 8.5 |
|  | BSA_F3 | 8.5 | 8.5 |
| synthetic AS1C peptides | Cas 1 | 6.4 | 43.6 |
|  | Cas 2 | 3.8 | 15.4 |
|  | Cas 3 | 2.6 | 46.2 |
|  | Cas 4 | 3.8 | 35.9 |
|  | Cas 5 | 5.1 | 41.0 |
|  | Cas 6 | 7.7 | 37.2 |

The vast majority of the tested milk components like cow's and goats milk, purified natural beta-lactoglobulin variant A and B (BLGA and BLGB) and the recombinant alphaS1- and (rAS1C) alphaS2-casein (rAS2C) showed about two times higher percentages of IgE reactivity than biological activity. Such findings can be explained by the presence of IgE binding epitopes, which are able to bind IgE, but are not able to cross-link receptor, bound IgE and trigger the release of mediators. Only in case of five components (recombinant BSA fragment 3 (F3), recombinant alpha-lactalbumin (rALA), cow casein fraction (CC), natural purified kappa-(KC) and beta-casein (BC)) the percentages of IgE reactivity and the biological activity reached similar values. The extent of degranulation with the synthetic alphaS1-casein-derived peptides was rather low ranging from about a tenth (Cas 3, Cas 4, Cas 5) to one fourth (Cas 2, Cas 6) of the activity of the complete protein.

It was found that many of the IgE-reactive alphaS1-casein peptides could not induce degranulation in the basophil release assay and thus represent IgE-reactive haptens. Thus, these peptides (haptens) are non-allergenic. This result implies that exclusive IgE testing would lead to the false positive conclusions regarding allergenicity assessment. On the other hand IgE-reactive haptens may be useful as therapeutic agents to saturate mast cell-bound IgE prior to allergen exposure and may be useful candidates for a safe immunotherapy of allergic diseases. AlphaS1-casein-derived peptides that bound IgE and triggered basophil release have been further identified and a few patients' sera were identified that did not show IgE reactivity to some peptides but induced basophil degranulation with these peptides. The latter result can be explained by the higher sensitivity of the basophil release assay.

In summary, comparison between measurements of IgE reactivity and biological activity reveals that the patients' sera show higher capacity in IgE binding than in the induction of basophil degranulation. The fact that allergenicity assays reflect the potential of a molecule to cause allergic symptoms implies that the measurement of IgE reactivity alone can not be used to identify with certainty allergenic components, but need to be complemented by a biological assay.

The combination of both assays, evaluation of IgE binding capacity and biological reactivity, allow to generate a data base containing allergenic proteins/fragments/peptides that can be detected by mass spectrometry. FIG. 4 shows a list of sequences of allergenic milk peptides and proteins which represents a prototype of such a data base. Milk components tested for serum IgE reactivity as for allergenic activity are listed. Information regarding the allergen names, the molecular weights (MW) in kilo Dalton (kDa), the function and preparation of the allergens as well as references are listed.

Experimental Protocol

Sera from 78 patients who were selected according to a positive case history, positive skin-prick reactions and determination of specific IgE to cow's milk extract using the CAP-FEIA System (Phadia, Uppsala, Sweden) were used. Sera were obtained from five adults and 73 children (30 female and 43 male) from Austria, Germany, Italy, Spain and France.

Purified proteins and casein fractions were purchased from Sigma Aldrich (St. Louis, US). Recombinant proteins and recombinant BSA fragments were expressed in *E. coli* as described by (Vrtala et al., 1997). AlphaS1-casein peptides were synthesized on an Applied Biosystems peptide synthesizer Model 433A as described (Focke et al., 2001)

Humanized Rat Basophil Leukaemia (RBL) cells (clone RBL-703/21) were incubated in microtiter plates overnight at 37° C. (7% $CO_2$, 95% humidity) with 50 µl human sera, diluted 1:10. Afterwards cells were washed and exposed to milk components, diluted to 0.3 µg/ml protein in Tyrodes buffer containing 50% $D_2O$ and 0.1% BSA/HAS for 1 hour at 37° C. (7% $CO_2$, 95% humidity). Spontaneous release of the cells was also evaluated. Finally, the cell supernatants were incubated with 50 µl assay solution (0.1 M citric acid or sodium citrate, pH 4.5, 160 µM 4-methyl umbelliferyl-N-acetyl-β-D-glucosaminide) in new microtiter plates at 37° C. (7% $CO_2$, 95% humidity) for 1 h. The reactions were stopped by addition of 100 µl glycine buffer per well and the fluorescence measured at $\lambda_{ex}$: 360 and $\lambda_{em}$: 465 using a fluorescence microplate reader. The specific hexosaminidase release of each sample was calculated using the formula: $[(Fl_S-Fl_{Sp}):(Fl_Z-Fl_{Sp})] \times 100$ (where $Fl_S$ is the fluorescence of the sample; $Fl_{Sp}$ is the fluorescence of the spontaneous release and $Fl_Z$ is the fluorescence of the total release).

Example 3

Identification of Proteins and/or Peptides with and without Allergenic Activity in Milk Samples and in Milk Derived Products by Mass Spectrometry A sequence database of allergenic milk proteins and peptides established by the combination of IgE reactivity and allergenic activity can serve as a basis for the development of a reliable, reproducible, analytical method for the assessment and prediction of allergenicity of milk samples and milk derived products. Mass spectrometry was used to detect potentially allergenic components in complex milk samples. As an example, mass spectrometry in combination with upstream high-performance liquid chromatography (HPLC) was applied for the analysis of a commercially available, extensively hydrolyzed hypoallergenic milk formula. Analysis of the chromatogram shown in FIG. 5 and the extracted mass spectra demonstrated that all proteins had been hydrolyzed to small peptides of a maximum length of 14 amino acids.

In particular, FIG. 5 shows the Separation of a hydrolyzed milk formula using nano liquid chromatography followed by electrospray ionization MS. Presentation of total ion chromatogram of 1 μg hydrolyzed milk sample. Retention times are shown on the x-axis and signal intensities in cps (counts per second) are displayed on the y-axis.

A database search using the MASCOT Search algorithms resulted in the identification of several small peptides of which three were identified as milk-derived allergen, namely beta-casein (Bos d 8 beta, FIG. 6). In FIG. 6 a Mascot search and the identification of beta-casein-derived peptides in hydrolyzed cow's milk is depicted. At the top beta-casein, the only identified milk allergen in mass spectrometry, is mentioned with its molecular mass and calculated pI. Below the search parameters and the obtained sequence coverage of beta-casein are given. The bottom displays the beta-casein sequence with the matched peptides printed in bold letters. The beta-casein allergen was identified with peptide matches: HQPHQPLPPT (calculated mass of 1.25 kDa, corresponding to aa 160-170 of beta-casein), VYPFPGPIPN (calculated mass of 1.19 kDa, corresponding to aa 74-84 of beta-casein), SSSEE (calculated mass of 0.65 kDa, corresponding to aa 31-36 of beta-casein), and PVVVPP (calculated mass of 0.87 kDa, corresponding to aa 96-103 of beta-casein). In FIG. 7 IgE reactivity testing of these peptides is shown (Table 1: cas b-1, 2, 3 and 4; FIG. 7). Beta-casein-derived peptides identified in hydrolyzed cow's milk are not IgE-reactive. IgE reactivity of nitrocellulose-dotted cow's milk (CM), recombinant beta-casein (rBC), synthetic beta-casein-derived peptides (cas b-1, cas b-2, cas b-3, cas b-4), and recombinant alphaS1-casein (rAS1C) were analysed by dot blot assay. Nitrocellulose-bound milk components were incubated with the sera from three cow's milk allergic patients (lanes 1, 2 and 3) and a non-allergic individual (lane C). Bound IgE antibodies were detected with $^{125}$I-labeled anti-IgE antibodies. This figure and these results show that they represent non-allergenic peptides, i.e. they were too short to bind IgE antibodies and could be discriminated from allergenic and IgE-reactive peptides as defined in the data base of IgE-reactive and allergenic cow's milk-derived peptides/proteins. Furthermore, they are different from the published major IgE binding regions of beta-casein (aa 1-16, aa 83-92, aa 135-144; Chatchatee 2001). None of the other IgE-reactive milk allergens and allergen fragments obtained by screening of the cDNA expression library (FIG. 1) were detected in the hydrolyzed milk sample which therefore could be identified as a non-allergenic preparation. Hence it was demonstrated—using extensively hydrolyzed milk—that LC-MS analysis can be used for the identification of non-allergenic milk preparations/samples.

TABLE 1

| Peptide | Sequence | Length (aa) | pI | MW (kDa) |
|---|---|---|---|---|
| A) Synthetic peptides of αS1-casein and BSA fragments. The name of the peptides, their amino acid sequence, length, pI and molecular weight in kDa are listed. | | | | |
| Cas1 | RPKHPIKHQGLPQEVLNENLLRFFVA PFPEVC | 32 | 8.22 | 3.75 |
| Cas2 | FGKEKVNELSKDIGSESTEDQAMEDI KQMEAES | 33 | 4.18 | 3.70 |
| Cas3 | ISSSEEIVPNSVEQKHIQKEDVPSER YLGYEQLLRC | 36 | 4.80 | 4.21 |
| Cas4 | CLKKYKVPQLEIVPNSAEERLHSMK EGIHIAQQKE | 34 | 8.14 | 3.96 |
| Cas5 | CPMIGVNQELAYFYPELFRQFYQLD AYPSGAWYYV | 35 | 4.14 | 4.24 |
| Cas6 | PLGTQYTDAPSFSDIPNPIGSENSE KTTMPLWC | 33 | 3.92 | 3.60 |
| BSA F1 | MRGVFRRDTHKSEIAHRFKDLGEEH FKGLVLIAFSQYLQQCPFDEHVKLVN ELTEFAKTCVADESHAGCEKSLHTLF GDELCKVASLRETYGDMADCCEKQ EPERNECFLSHKDDSPDLPKLKPDPN TLCDEFKADEKKFWGKYLYEIARRH PYFYAPELLYYANKYNGVFQECCQA EDKGACLLPKIETMREKVLTSSHHH HHH | 190 | 5.95 | 23.9 |
| BSA F2 | MARQRLRCASIQKFGERALKAWSV ARLSQKEPKAEFVEVTKLVTDLTKV HKECCHGDLLECADDRADLAKYICD NQDTISSKLKECCDKPLLEKSHCIAE VEKDAIPENLPPLTADFAEDKDVCK NYQEAKDAFLGSFLYEYSRRHPEYA VSVLLRLAKEYEATLEECCAKDDPH ACYSTVFDKLKHLVDEHHHHHH | 189 | 5.94 | 22.6 |
| BSA F3 | MPQNLIKQNCDQFEKLGEYGFQNAL IVRYTRKVPQVSTPTLVEVSRSLGKV GTRCCTKPESERMPCTEDYLSLWNR LCVLHEKTPVSEKVTKCCTESLVNR RPCFSALTPDETYVPKAFDEKLFTFH ADICTLPDTEKQIKKQTALVELLKHK PKATEEQLKTVMENFVAFVDKCCA ADDKEACFAVEGPKLVVSTQTALAH HHHHH | 200 | 7.54 | 23.4 |
| B) Synthetic peptides of β-casein. The name of the peptides, their amino acid sequence, length, pI and molecular weight in kDa are listed. | | | | |
| cas b-1 | HQPHQPLPPTV | 11 | 6.92 | 1.25 |
| cas b-2 | VYPFPGPIIPNS | 11 | 5.49 | 1.19 |
| cas b-3 | LSSSEE | 6 | 4.24 | 0.65 |
| cas b-4 | PVVVPPFL | 8 | 5.96 | 0.87 |

Experimental Protocol

Hydrolyzed milk formula was analyzed by reversed-phase HPLC using a nano liquid chromatography system (Ultimate, LC Packings Dionex, The Netherlands) connected to the nanospray interface of a HCT-Ultra mass spectrometer (Bruker Daltonik, Germany). The obtained mass spectra were searched against the SwissProt protein databank using MASCOT (Matrix Science, London, United Kingdom) software search algorithms. For dot blot analysis 1 μg of protein was dotted onto nitrocellulose, and incubated with sera from milk allergic patients diluted 1:20 in PBST (PBS, 0.5% v/v Tween 20). Bound IgE antibodies were detected with 1:15 diluted $^{125}$I-labelled anti-human IgE antibodies (IBL, Germany).

Example 4

Epitope Mapping of Bovine Alpha-Lactalbumin (ALA) to Identify IgE Reactive ALA-Derived Peptides Methods Synthesis of ALA-derived peptides: ALA-derived peptides (Lac1-Lac8) displayed in Table I were synthesized using the Fmoc (9 fluorenyl methoxy carbonyl)-strategy with HBTU [(2-/1H-Benzotriazol-1-yl)1,1,3,3, tetramethyluronium hexafluorophosphat]-activation (0.1 mmol small-scale cycles) on an Applied Biosystems peptide synthesizer Model 433A (Foster City, Calif.) and purified as described (Focke et al., Faseb J 15:2042-2044).

IgE reactivity testing to ALA-derived peptides: IgE reactivities of the ALA-derived peptides were determined by microarray analysis as described (Schulmeister et al., J Immunol. 182(11):7019-29). In brief, milk components were spotted onto a capillary-flow membrane on an ordinary microscope glass slide and incubated with 25 μl of patients' sera. Bound IgE antibodies were detected with a fluorescence-conjugated anti-IgE antibody at a wavelength of 670 nm. The cut off level was set for each patient as the double value of the individual value gained with human serum albumin.

Results

Identification of ALA Epitopes which are Reactive with IgE Antibodies

In order to identify IgE-reactive epitopes of ALA, we synthesized 8 peptides spanning the ALA sequence (Table 2). The 8 peptides had a length of 19-20 amino acids with 5 amino acid overlaps. The IgE reactivity of the 8 overlapping peptides was evaluated by microarray analysis using sera from the 36 patients showing IgE reactivity to rALA. We found that 30.6% of the patients reacted to Lac1, 33.3% to Lac2, 5.6% to Lac4, 2.8% to Lac5, Lac6, and Lac7, and 11.1% to Lac8 (Table 3). In total 19 of the 36 patients with IgE reactivity to rALA reacted at least with one ALA-derived synthetic peptide.

TABLE 2

Synthetic ALA-derived peptides$^a$

| Peptide | Sequence | Length (aa) | pI | MW (kDa) |
|---|---|---|---|---|
| Lac1 | EQLTKCEVFRELKDLKGYG | 19 | 6.34 | 2.26 |
| Lac2 | LKGYGGVSLPEWVCTTFHTS | 20 | 6.74 | 2.18 |
| Lac3 | TFHTSGYDTQA1YQNNDSTE | 20 | 4.31 | 2.23 |
| Lac4 | NDSTEYGLFQINNK1WCKDD | 20 | 4.42 | 2.40 |
| Lac5 | WCKDDQNPHSSNICNISCDK | 20 | 5.30 | 2.31 |
| Lac6 | ISCDKFLDDDLTDDIMCVKK | 20 | 4.11 | 2.32 |
| Lac7 | MCVKKILDKVGINYWLAHKA | 20 | 9.52 | 2.33 |
| Lac8 | LAHKALCSEKLDQWLCEKL | 19 | 6.74 | 2.23 |

$^a$Abbreviations used in the table: Lac1-Lac8, ALA-derived peptides 1-8; aa, amino acids; pI, isoelectric point; MW, molecular weight; kDa, kilo Dalton.

TABLE 3

IgE binding capacity of alpha-lactalbumin-derived peptides tested with sera from the 36 patients with IgE reactivity to rALA

| n = 36 | | IgE binding (% of patients) |
|---|---|---|
| recombinant ALA | rALA | 100.0 |
| synthetic ALA peptides | Lac1 | 30.6 |
| | Lac2 | 33.3 |
| | Lac3 | 0 |
| | Lac4 | 5.6 |
| | Lac5 | 2.8 |
| | Lac6 | 2.8 |
| | Lac7 | 2.8 |
| | Lac8 | 11.1 |

The disclosure furthermore comprises the following items:
1. Method for identifying allergenic proteins and peptides encoded by a DNA or cDNA expression library comprising the steps of:
   a) providing at least one expression library comprising DNA or cDNA derived from at least one allergen source,
   b) expressing at least one protein or peptide encoded by said expression library,
   c) determining the binding capacity of said at least one protein or peptide to IgE of at least one serum of an individual who is sensitive to the at least one allergen source,
   d) contacting the at least one protein or peptide exhibiting an IgE binding capacity as determined in step c) with basophil cells or mast cells and
   e) identifying the at least one protein or peptide as being allergenic when said basophil cells release upon contact with at least one protein or peptide of step d) at least one mediator.
2. Method according to item 1, wherein the at least one allergen source is an animal.
3. Method according to item 2, wherein the animal is a mammal.
4. Method according to item 3, wherein the mammal is a cow.
5. Method according to item 3, wherein the mammal is a cat.
6. Method according to item 3, wherein the mammal is a dog.
7. Method according to item 2, wherein said mammal is a lactating mammal and the DNA or cDNA is obtained from the mammary gland tissue.
8. Method according to item 2, wherein the animal is a mite.
9. Method according to item 1, wherein the animal is a fish.
10. Method according to item 2, wherein the allergen source is an egg.
11. Method according to item 1, wherein the at least one allergen source is a plant.
12. Method according to item 11, wherein the plant is a weed.
13. Method according to item 11, wherein the plant is a nut.
14. Method according to item 11, wherein the plant is a tree.
15. Method according to item 1, wherein the expression library is a phage display library or a bacterial expression library.
16. Method according to item 1, wherein the IgE binding capacity is determined by immobilizing the at least one protein or peptide on a solid support, contacting the solid support with IgE and detecting binding of IgE on said solid support.

17. Method according to item 1, wherein the basophil cells are humanized rat basophil leukaemia (RBL) cells (clone RBL-703/21).
18. Method according to item 1, wherein the amino acid sequence of the at least one protein or peptide exhibiting an IgE binding capacity as determined in step c) is determined and the at least one protein or peptide chemically synthesized or recombinantly produced prior to step d).
19. Method according to item 1, wherein the method further comprises a step of determining the amino acid sequence of the at least one protein or peptide identified in step e).
20. Method according to item 19, wherein the amino acid sequence is determined by mass spectrometry.
21. Method according to item 19, wherein the amino acid sequence is determined by Edman degradation.

All cited patents and publications referred to in this application are incorporated herein by reference.

The invention thus being described, it will be apparent that it may be varied in many ways. Such variations are not to be regarded as a departure from the spirit and scope of the present invention and all such modifications as would be obvious to one skilled in the art are intended to be included in the scope of the following claims.

The invention claimed is:

1. A method for identifying allergenic milk alphaS1-, alphaS2-, beta- or kappa-casein proteins and/or peptides, the method comprising the steps of:
   a) providing at least one expression library comprising DNA or cDNA derived from the mammary gland tissue of a lactating cow,
   b) expressing at least one alphaS1-, alphaS2-, beta- or kappa-casein protein or peptide encoded by said expression library,
   c) determining the binding capacity of said at least one alphaS1-, alphaS2-, beta- or kappa-casein protein or peptide to IgE of at least one serum of an individual who is sensitive to cow's milk, wherein the binding capacity to IgE is indicative of an allergy or a predisposition to an allergy,
   d) contacting the at least one alphaS1-, alphaS2-, beta- or kappa-casein protein or peptide exhibiting an IgE binding capacity as determined in step c) with basophil cells, eosinophil cells or mast cells, wherein the basophil cells, eosinophil cells or mast cells are loaded with IgE from at least one serum of individual who sensitive to cow's milk and
   e) identifying the at least one alphaS1-, alphaS2-, beta- or kappa-casein protein or peptide as being allergenic when said basophil cells, eosinophil cells or mast cells release at least one mediator upon contact with at least one alphaS1-, alphaS2-, beta- or kappa-casein protein or peptide of step d).

2. The method according to claim 1, wherein the method further comprises a step of determining the amino acid sequence of the at least one alphaS1-, alphaS2-, beta- or kappa-casein protein or peptide identified in step e).

3. A method for identifying a IgE-reactive non-allergenic milk alphaS1-, alphaS2-, beta- or kappa-casein protein or peptide encoded by a DNA or cDNA of at least one expression library comprising the steps of:
   a) providing at least one expression library comprising DNA or cDNA derived from the mammary gland tissue of a lactating cow,
   b) expressing at least one alphaS1-, alphaS2-, beta- or kappa-casein protein or peptide encoded by said expression library,
   c) determining the binding capacity of said at least one alphaS1-, alphaS2-, beta- or kappa-casein protein or peptide to IgE of at least one serum of an individual who is sensitive to cow's milk, wherein the binding capacity to IgE is indicative of an allergy or a predisposition to an allergy,
   d) contacting the at least one alphaS1-, alphaS2-, beta- or kappa-casein protein or peptide exhibiting an IgE binding capacity as determined in step c) with basophil cells, eosinophil cells or mast cells, wherein the basophil cells, eosinophil cells or mast cells are loaded with IgE from at least one serum of individual who sensitive to cow's milk and
   e) determining if said basophil cells, eosinophil cells or mast cells
      (i) release upon contact with the at least one alphaS1-, alphaS2-, beta- or kappa-casein protein or peptide at least one mediator, or
      (ii) degranulate upon contact with the at least one alphaS1-, alphaS2-, beta- or kappa-casein protein or peptide,
         wherein the lack of (i) release upon contact with the at least one protein or peptide at least one mediator and (ii) degranulation upon contact with the at least one protein or peptide, indicates that the protein or peptide is an IgE reactive non-allergenic protein or peptide.

4. The method of claim 1, further comprising the step of identifying the presence of the at least one alphaS1-, alphaS2-, beta- or kappa-casein protein and peptide in a sample comprising a milk protein by mass spectrometry.

5. The method of claim 4, wherein the proteins and peptides present in the sample are isolated prior mass spectrometry.

6. The method of claim 4, wherein the proteins and peptides present in the sample are isolated by an electrophoretic method.

7. The method of claim 6, wherein the electrophoretic method is two-dimensional electrophoresis.

8. The method of claim 4, wherein the proteins and peptides present in the sample are isolated by high performance liquid chromatography.

9. The method of claim 3, further comprising the step of identifying the presence of the at least one alphaS1-, alphaS2-, beta- or kappa-casein protein and peptide in a sample comprising a milk protein by mass spectrometry.

10. The method of claim 9, wherein the proteins and peptides present in the sample are isolated prior mass spectrometry.

11. The method of claim 9, wherein the proteins and peptides present in the sample are isolated by an electrophoretic method.

12. The method of claim 11, wherein the electrophoretic method is two-dimensional electrophoresis.

13. The method of claim 9, wherein the proteins and peptides present in the sample are isolated by high performance liquid chromatography.

* * * * *